US 8,697,868 B2

(12) United States Patent
Himmelsbach et al.

(10) Patent No.: US 8,697,868 B2
(45) Date of Patent: Apr. 15, 2014

(54) 8-[3-AMINO-PIPERIDIN-1-YL]-XANTHINES, THEIR PREPARATION AND THEIR USE AS PHARMACEUTICAL COMPOSITIONS

(75) Inventors: Frank Himmelsbach, Mittelbiberach (DE); Elke Langkopf, Warthausen (DE); Matthias Eckhardt, Biberach (DE); Mohammad Tadayyon, Watford (GB); Leo Thomas, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 426 days.

(21) Appl. No.: 12/360,392

(22) Filed: Jan. 27, 2009

(65) Prior Publication Data

US 2009/0137801 A1    May 28, 2009

Related U.S. Application Data

(63) Continuation of application No. 11/060,703, filed on Feb. 17, 2005, now Pat. No. 7,501,426.

(60) Provisional application No. 60/551,108, filed on Mar. 8, 2004, provisional application No. 60/562,573, filed on Apr. 15, 2004.

(30) Foreign Application Priority Data

Feb. 18, 2004  (DE) .......................... 10 2004 008 112
Mar. 17, 2004  (DE) .......................... 10 2004 012 921
Jul. 3, 2004    (DE) .......................... 10 2004 032 263

(51) Int. Cl.
*C07D 473/00* (2006.01)
*C07D 473/02* (2006.01)
*C07D 473/04* (2006.01)

(52) U.S. Cl.
USPC ............................ 544/272; 544/269; 544/270

(58) Field of Classification Search
USPC ................................. 544/268, 269, 270, 272
See application file for complete search history.

(56) References Cited

U.S. PATENT DOCUMENTS

| | | | |
|---|---|---|---|
| 2,056,046 A | 9/1936 | Fourneau |
| 2,375,138 A | 5/1945 | Salvin |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender |
| 4,061,753 A | 12/1977 | Bodor et al. |
| 4,599,338 A | 7/1986 | Regnier et al. |
| 4,639,436 A | 1/1987 | Junge et al. |
| 4,687,777 A | 8/1987 | Meguro et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens |
| 5,051,517 A | 9/1991 | Findeisen |
| 5,084,460 A | 1/1992 | Munson, Jr. et al. |
| 5,219,870 A | 6/1993 | Kim |
| 5,223,499 A | 6/1993 | Greenlee |
| 5,234,897 A | 8/1993 | Findeisen et al. |
| 5,258,380 A | 11/1993 | Janssens |
| 5,266,555 A | 11/1993 | Findeisen et al. |
| 5,273,995 A | 12/1993 | Roth |
| 5,300,298 A | 4/1994 | LaNoue |
| 5,329,025 A | 7/1994 | Wong et al. |
| 5,332,744 A | 7/1994 | Chakravarty et al. |

(Continued)

FOREIGN PATENT DOCUMENTS

AU    2003280680 A1    6/2004
AU    2009224546 A1    9/2009

(Continued)

OTHER PUBLICATIONS

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Brittain, H.G., "Methods for the Characterization of Polymorphs: X-Ray Powder Diffraction," Polymorphism in Pharmaceutical Solids, 1999, p. 235-238.

(Continued)

*Primary Examiner* — Kortney L Klinkel
*Assistant Examiner* — John Mauro
(74) *Attorney, Agent, or Firm* — Michael P. Morris; Timothy X. Witkowski

(57) ABSTRACT

Disclosed are substituted xanthines of the formula (I)

wherein R is defined as in claim 1, the tautomers, the stereoisomers, the mixtures thereof and the salts thereof, which have valuable pharmacological properties, particularly an inhibiting effect on the activity of the enzyme dipeptidylpeptidase-IV (DPP-IV).

8 Claims, No Drawings

(56) References Cited

U.S. PATENT DOCUMENTS

| | | |
|---|---|---|
| 5,389,642 A | 2/1995 | Dorsch |
| 5,399,578 A | 3/1995 | Buhlmayer et al. |
| 5,407,929 A | 4/1995 | Takahashi et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kuefner-Muhl et al. |
| 5,728,849 A | 3/1998 | Bouchard et al. |
| 5,753,635 A | 5/1998 | Buckman |
| 5,830,908 A | 11/1998 | Grunenberg et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,248,758 B1 | 6/2001 | Klokkers et al. |
| 6,303,661 B1 | 10/2001 | Demuth |
| 6,342,601 B1 | 1/2002 | Bantick |
| 6,372,940 B1 | 4/2002 | Cavazza |
| 6,548,481 B1 | 4/2003 | Demuth et al. |
| 6,579,868 B1 | 6/2003 | Asano |
| 6,727,261 B2 | 4/2004 | Gobbi et al. |
| 6,784,195 B2 | 8/2004 | Hale et al. |
| 6,821,978 B2 | 11/2004 | Chackalamannil |
| 6,869,947 B2 | 3/2005 | Kanstrup |
| 6,995,183 B2 | 2/2006 | Hamann et al. |
| 7,060,722 B2 | 6/2006 | Kitajima |
| 7,074,794 B2 | 7/2006 | Kitajima |
| 7,074,798 B2 | 7/2006 | Yoshikawa |
| 7,074,923 B2 | 7/2006 | Dahanukar |
| 7,109,192 B2 | 9/2006 | Hauel |
| 7,179,809 B2 | 2/2007 | Eckhardt |
| 7,183,280 B2 | 2/2007 | Himmelsbach |
| 7,192,952 B2 | 3/2007 | Kanstrup |
| 7,217,711 B2 | 5/2007 | Eckhardt |
| 7,235,538 B2 | 6/2007 | Kanstrup et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,645,763 B2 | 1/2010 | Himmelsbach et al. |
| 7,718,666 B2 | 5/2010 | Boehringer et al. |
| 7,799,782 B2 | 9/2010 | Munson et al. |
| 7,820,815 B2 * | 10/2010 | Pfrengle et al. ............... 544/268 |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup |
| 2002/0169174 A1 | 11/2002 | Chackalamannil et al. |
| 2002/0198205 A1 | 12/2002 | Himmelsbach |
| 2003/0078269 A1 | 4/2003 | Pearson et al. |
| 2003/0100563 A1 | 5/2003 | Edmondson et al. |
| 2003/0105077 A1 | 6/2003 | Kanstrup et al. |
| 2003/0114390 A1 | 6/2003 | Washburn et al. |
| 2003/0149071 A1 | 8/2003 | Gobbi et al. |
| 2003/0166578 A1 | 9/2003 | Arch et al. |
| 2003/0199528 A1 | 10/2003 | Kanstrup |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa |
| 2004/0087587 A1 | 5/2004 | Himmelsbach |
| 2004/0097510 A1 | 5/2004 | Himmelsbach et al. |
| 2004/0116328 A1 | 6/2004 | Yoshikawa et al. |
| 2004/0122228 A1 | 6/2004 | Maier |
| 2004/0126358 A1 | 7/2004 | Warne et al. |
| 2004/0138214 A1 | 7/2004 | Himmelsbach et al. |
| 2004/0138215 A1 | 7/2004 | Eckhardt |
| 2004/0166125 A1 | 8/2004 | Himmelsbach |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa |
| 2006/0074058 A1 | 4/2006 | Holmes et al. |
| 2006/0079541 A1 | 4/2006 | Langkopf |
| 2006/0094722 A1 | 5/2006 | Yasuda |
| 2006/0100199 A1 | 5/2006 | Yoshikawa |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima |
| 2006/0205711 A1 | 9/2006 | Himmelsbach |
| 2006/0205943 A1 | 9/2006 | Dahanukar et al. |
| 2006/0247226 A1 | 11/2006 | Himmelsbach |
| 2006/0270668 A1 | 11/2006 | Chew et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0259900 A1 | 11/2007 | Sieger |
| 2007/0259925 A1 | 11/2007 | Boehringer et al. |
| 2007/0281940 A1 | 12/2007 | Dugi |
| 2007/0299076 A1 | 12/2007 | Piotrowski et al. |
| 2008/0039427 A1 | 2/2008 | Ray et al. |

(56) References Cited

U.S. PATENT DOCUMENTS

| | | |
|---|---|---|
| 2008/0107731 A1 | 5/2008 | Kohlrausch |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0325926 A1 | 12/2009 | Himmelsbach |
| 2010/0092551 A1 | 4/2010 | Nakamura et al. |
| 2010/0173916 A1 | 7/2010 | Himmelsbach et al. |
| 2010/0183531 A1 | 7/2010 | Johncock et al. |
| 2010/0204250 A1 | 8/2010 | Himmelsbach et al. |
| 2011/0009391 A1 | 1/2011 | Braun et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2013/0172244 A1 | 7/2013 | Klein et al. |
| 2013/0184204 A1 | 7/2013 | Pfrengle et al. |

FOREIGN PATENT DOCUMENTS

| | | |
|---|---|---|
| CA | 1123437 A1 | 5/1982 |
| CA | 2136288 A1 | 5/1995 |
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0400974 A2 | 5/1990 |
| EP | 0389282 A2 | 9/1990 |
| EP | 0399285 A1 | 11/1990 |
| EP | 409281 A1 | 1/1991 |
| EP | 0412358 A1 | 2/1991 |
| EP | 443983 A1 | 8/1991 |
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1557165 A1 | 7/2005 |
| EP | 1537880 A1 | 8/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 2143443 A1 | 1/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| JP | S37-4895 | 6/1962 |
| JP | 770120 | 3/1995 |
| JP | 2001213770 A | 8/2001 |
| JP | 2003/300977 | 10/2003 |
| JP | 2006/045156 | 2/2006 |
| KR | 20070111099 A | 11/2007 |
| WO | 91/07945 A1 | 6/1991 |
| WO | 9205175 A1 | 4/1992 |
| WO | 94/03456 A1 | 2/1994 |
| WO | 9402150 A1 | 2/1994 |
| WO | 9609045 A1 | 3/1996 |
| WO | 9636638 A1 | 11/1996 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9822464 A1 | 5/1998 |
| WO | 9840069 A2 | 9/1998 |
| WO | 9856406 A1 | 12/1998 |
| WO | 99/29695 A1 | 6/1999 |
| WO | 9950248 A1 | 10/1999 |
| WO | 0073307 A2 | 12/2000 |
| WO | 0107441 A1 | 2/2001 |
| WO | 0140180 A2 | 6/2001 |
| WO | 0152825 | 7/2001 |
| WO | 0152852 A1 | 7/2001 |
| WO | 0168646 A1 | 9/2001 |
| WO | 0177110 A1 | 10/2001 |
| WO | 0197808 A1 | 12/2001 |
| WO | 02/02560 A2 | 1/2002 |
| WO | 02/14271 A1 | 2/2002 |
| WO | 02/24698 A1 | 3/2002 |
| WO | 02053516 A2 | 7/2002 |

(56) References Cited

FOREIGN PATENT DOCUMENTS

| | | |
|---|---|---|
| WO | 02/068420 A1 | 9/2002 |
| WO | 03/004496 A1 | 1/2003 |
| WO | 03000241 A2 | 1/2003 |
| WO | 03002531 A2 | 1/2003 |
| WO | 03004496 A1 | 1/2003 |
| WO | 03/024965 A2 | 3/2003 |
| WO | 03037327 A1 | 5/2003 |
| WO | 03/057200 A2 | 7/2003 |
| WO | 03055881 A1 | 7/2003 |
| WO | 03064454 A1 | 8/2003 |
| WO | 03088900 A2 | 10/2003 |
| WO | 03/104229 A1 | 12/2003 |
| WO | 03099279 A1 | 12/2003 |
| WO | 03099836 A1 | 12/2003 |
| WO | 03106428 A1 | 12/2003 |
| WO | 2004011416 A1 | 2/2004 |
| WO | 2004/018467 A2 | 3/2004 |
| WO | 2004/018468 A2 | 3/2004 |
| WO | 2004018469 A1 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/050658 A1 | 6/2004 |
| WO | 2004052362 A1 | 6/2004 |
| WO | 2004062689 A1 | 7/2004 |
| WO | 2004065380 A1 | 8/2004 |
| WO | 2004081006 A1 | 9/2004 |
| WO | 2004/096806 A1 | 11/2004 |
| WO | 2004096811 A1 | 11/2004 |
| WO | 2004/108730 A1 | 12/2004 |
| WO | 2004/111051 A1 | 12/2004 |
| WO | 2004106279 A2 | 12/2004 |
| WO | 2005000846 A1 | 1/2005 |
| WO | 2005000848 A1 | 1/2005 |
| WO | 2005007647 A1 | 1/2005 |
| WO | 2005012288 A1 | 2/2005 |
| WO | 2005023179 A2 | 3/2005 |
| WO | 2005/058901 A1 | 6/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005/082906 A1 | 9/2005 |
| WO | 2005/085246 A1 | 9/2005 |
| WO | 2005082906 A1 | 9/2005 |
| WO | 2005092870 A1 | 10/2005 |
| WO | 2005092877 A1 | 10/2005 |
| WO | 2005095343 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006/029769 A1 | 3/2006 |
| WO | 2006027204 A1 | 3/2006 |
| WO | 2006036664 A1 | 4/2006 |
| WO | 2006040625 A1 | 4/2006 |
| WO | 2006/048427 A1 | 5/2006 |
| WO | 2006047248 A1 | 5/2006 |
| WO | 2006048209 A1 | 5/2006 |
| WO | 2006/068163 A1 | 6/2006 |
| WO | 2006071078 A1 | 7/2006 |
| WO | 2006076231 A2 | 7/2006 |
| WO | 2006083491 A2 | 8/2006 |
| WO | 2006135693 A2 | 12/2006 |
| WO | 2006137085 A1 | 12/2006 |
| WO | 2007007173 A2 | 1/2007 |
| WO | 2007/017423 A2 | 2/2007 |
| WO | 2007014886 A1 | 2/2007 |
| WO | 2007014895 A2 | 2/2007 |
| WO | 2007033350 A1 | 3/2007 |
| WO | 2007035355 A2 | 3/2007 |
| WO | 2007035665 A1 | 3/2007 |
| WO | 2007041053 A2 | 4/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007137107 A2 | 11/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008/017670 A1 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008131149 A2 | 10/2008 |
| WO | 2009011451 A | 1/2009 |
| WO | 2009022007 A1 | 2/2009 |
| WO | 2009022008 A1 | 2/2009 |
| WO | 2009022010 A1 | 2/2009 |
| WO | 2009024542 A2 | 2/2009 |
| WO | 2009063072 A2 | 5/2009 |
| WO | 2009099734 A1 | 8/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010147768 A1 | 12/2010 |
| WO | 2011039367 A2 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2012065993 A1 | 5/2012 |
| WO | 2013103629 A1 | 7/2013 |

OTHER PUBLICATIONS

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

(56) References Cited

OTHER PUBLICATIONS

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Januvia; Patient Information; Oct. 2007.

Office Action for U.S. Appl. No. 10/695,597 mailed May 2, 2008.

Patani George A. et al.: "Bioisoterism : A Rational Approach in Drug Design", Chemical Reviews, 1996, vol. 96, No. 8, pp. 3147-3176.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

White, J.R; "Dipeptidyl Peptidase-IV Inhibitors: Pharmacological Profile and Clinical Use" Clinical Diabetes, 2008, vol. 26, No. 2, pp. 53-57.

Wolff, M.E.: "Burger's Medicinal Chemistry and Drug Discovery" Fifth Edition, vol. 1: Principles and Practice, pp. 975-977, 1994, John Wiley & Sons, Inc.

Zejc, Alfred et al; Badania Nad Piperazynowymi Pochodnymi Dwumetyloksantyn; Acta Polon. Pharm. XXXV. Nr 4, 1976, pp. 417-421.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors, 2003.

International Search Report for PCT/EP03/09127 mailed Nov. 28, 2003.

International Search Report for PCT/EP2007/054270 mailed Aug. 14, 2007.

International Search Report for PCT/EP2007/054204 mailed Aug. 3, 2007.

Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Salomon, J., et al; Ultraviolet and g-Ray-Induced Reactions of Nucleic Acid Constituents. Reactions of Purines with Amines; Photochemistry and Photobiology (1974) vol. 19 pp. 21-27.

Sathananthan, A., et al., "Personalized pharmacotherapy for type 2 diabetes mellitus". Personalized Medicine 2009 Future Medicine Ltd, vol. 6, No. 4, Jul. 2009, p. 417-422.

Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Stahl, P.H., "Handbook of Pharmaceutical Salts". C.G. Wermuth, Wiley-VCH, 2002, p. 61.

Sune Negre, J. M. "New Galenic Contributions to Administration Forms". Continued Training for Hospital Pharmacists 3.2. [retrieved on Feb. 23, 2011]. Retrieved from the internet <http://www.ub.es/legmh/capitols/sunyenegre.pdf>.

Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.

Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.

Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, American Socity for Therapeutics, US, vol. 325, No. 1, Apr. 1, 2008, pp. 175-182 abstract p. 177, col. 2, paragraph 1 table 1 p. 1B1, col. 2, last paragraph-p. 182, col. 1.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.

X-Ray Diffraction. The United States Pharmacopeia, 2002, USP 25 NF20, p. 2088-2089.

(56) References Cited

OTHER PUBLICATIONS

Yasuda, et al. "E3024 3-but-2-ynyl-5-methyl-2-piperazin-1-yl-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Levien,T.L. et al, "New drugs in development for the treatment of diabetes", Diabetes Spectrum, American Diabetes Association, US, vol. 22, No. 2, Jan. 1, 2009, pp. 92-106.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
Bastin, R.J. et al., "Salt Selection and Optimization Procedures for Pharmaceutical New Chemical Entities". Organic Process Research and Development, 2000, vol. 4, p. 427-435.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Abstract in English for German DE2205815, 1972.
Abstract in English for German EP0023032, 1981.
Abstract in English, for KR20070111099, Nov. 11, 2007.
Ahren B: "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determinatio of the enantiomeric composition of thalidomide solutions by electrospray ionizatio tandem mass spectrometry". Chem Comm, 2002, p. 2242-2243.
Aulinger, B.A. et al., "Ex-4 and the DPP-IV Inhibitor Vildagliptin have Additive Effects to Suppress Food Intake in Rodents". Abstract No. 1545-P, 2008.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Bundgaard, H. "Design of prodrugs: Bioreversible derivatives for various functional groups and chemical entities". Royal Danish School of Pharmacy, 1985, p. 1-92.
Chemical Abstract. EP412358, 1991:185517, Findeisen.
Chemical Abstract: FR2707641, 1995:543545, Dodey.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].
Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/tria1/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.
Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.
Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.
Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

(56) References Cited

OTHER PUBLICATIONS

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.
Gallwitz, B. et al., "Saxagliptin, a dipeptidyl peptidase IV inhibitor for the treatment of type 2 diabetes". IDRUGS, vol. 11, No. 12, Dec. 2008, p. 906-917.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Giron, D.; Thermal Analysis and Calorimetric Methods in the Characterisation of Polymorphs and Solvates; Thermochimica Acta (1995) vol. 248 pp. 1-59.
Graefe-Mody et al., "The novel DPP-4 inhibitor . . . " Diabetes, (online) 2008, XP002561421 http://professional.diabetes.org/content/posters/2008/p553.pdf.
Greene, T.W, et al., "Protection for the Amino Group". Protective Groups in Organic Synthesis, 3rd edition, 1999, p. 494-653.
Gwaltney, S. "Medicinal Chemistry Approaches to the Inhibition of Dipeptidyl Peptidase IV", Current Topics in Medicinal Chemistry, 2008, 8, p. 1545-1552.
He, Y.L. et al., "The influence of hepatic impairment on the pharmacokinetics f the dipeptidyl peptidase IV (DPP-4) inhibitor vildagliptin" European Journal of Clinical Pharmacology, vol. 63, No. 7, May 8, 2007, p. 677-686.
Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.
International Search Report for PCT/EP2005/001427 mailed May 23, 2005.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kanada, S. et al., "Safety, tolerability, pharmacokenetics and pharmacodynamics of multiple doses of BI 1356 (proposed tradename Ondero), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.
Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.
Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.
March, J. "Advanced Organic Chemistry: Reactions, Mechanisms, and Structure". Fourth Edition, 1992, pp. 652-653.
Mendes, F.D, et al. "Recent advances in the treatment of non-alcoholic fatty liver disease". Expert Opinion on Investigational Drugs, vol. 14, No. 1, Jan. 1, 2005, p. 29-35.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Anstee, Quentin M. et al. "Mouse models in non-alcholic fatty liver disease and steatohepatitis research" (2006) International Journal of Expermental Pathology, vol. 87, pp. 1-16.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Deacon, Carolyn F. et al. "Linaglipitn, a xanthine-based dipeptidyl peptidase-4 inhibitor with an unusual profile for the treatment of type 2 diabetes" Expert Opin. Investig. Drugs (2010) 19(1): 133-140.
Demuth, H-U. et al., "Type 2 diabetes—Therapy with dipeptidyl peptidase IV inhibitors". Biochimica et Biophysica Acta, vol. 1751(1), 2005, p. 33-44.
European Search Report for EP 08 15 9141 mailed Apr. 6, 2009 (European counterpart of U.S. Appl. No. 12/143,128).
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Hayashi, Michio., "Recipe for Oral Hypoglycemic Agents to Pathological Condition" Pharmacy (2006) vol. 57, No. 9 pp. 2735-2739.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.

(56) References Cited

OTHER PUBLICATIONS

Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.

Hunziker, D. et al, "Inhibitors of DPP IV—recent advances and structural views", Current Topics in Medicinal Chemistry, 2005, vol. 5 issue 16, pp. 1623-1637.

Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.

International Search Report and Written Opinion for PCT/EP2011/057256 mailed Jul. 22, 2011.

International Search Report and Written Opinion for PCT/EP2012/063852 mailed Sep. 6, 2012.

International Search Report for PCT/EP03/12821 mailed Mar. 30, 2004.

International Search Report for PCT/EP03/13648 mailed Apr. 5, 2004.

International Search Report for PCT/EP2007/058181 mailed Nov. 28, 2007.

Kharkevich, D. A., "Educational Literature" Pharmacology (1987) Third Edition, Meditsina Press, Moscow pp. 47-48.

Kibbe, A.H., Handbook of Pharmaceutical Excipients, 3rd Edition, pp. 104-107.

Kibbe, Editor. Handbook of Pharmaceuticals Excipiets, Third Edition, Copovidon—pp. 196-197, Date of Revision: Dec. 16, 2008. Mannitol—pp. 424-425, Date of Revision: Feb. 19, 2009.

Kim, Kwang-Rok et al. "KR-62436, 6-{2-[2-(5-cyano-4,5-dihydropyrazol-1-yl)-2-oxoethylamino]ethylamino} nicotinonitrile, is a novel dipeptidyl peptidase-IV (DPP-IV) inhibitor with anti-hyperglycemic activity" European Journal of Pharmacology 518 (2005) pp. 63-70.

Komori, Kiyoshi., "Treatment of Diabetes in Patients for Whom Metforming Treatment is Not Appropriate" Modern Physician (2008) vol. 27, No. 2 pp. 163-165.

Matsumiya, Teruhiko, et al., "Therapeutic Drugs for Clinicians" Diagnosis and Treatment (2008) vol. 96, No. 2 pp. 389-390.

Mayo Clinic Staff: "Nonalchoholic fatty liver disease: Prevention" [retrieved on Nov. 30, 2012]. retrieved from the Internet: URL:http://www.mayoclinic.com/health/nonalcoholic-fatty-liver-disease/DS00577DSECTION=prevention>.

Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.

Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.

Plummer, C.J.G. et al., "The Effect of Melting Point Distributions on DSC Melting Peaks." Polymer Bulletin, 1996, vol. 36, pp. 355-360.

Sarafidis, Panteleimon et al. "Cardiometabolic Syndrome and Chronic Kidney Disease: What is the Link?" JCMS (2006) 1: pp. 58-65.

Shanks, N. et al., Are animal models predictive for humans?, PEHM, Philosophy, Ethics, and Humanaities in Medicine, 4(2), 2009, 1-20.

Shintani, Maki, et al., "Insulin Resistance and Genes" Circulatory Sciences (1997) vol. 17, No. 12 pp. 1186-1188.

Tounyoubyou, "Symposium-19: Future Perspectives on Incretion Therapy in Diabetes." 2008, vol. 51, Suppl. 1, p. S-71, S19-2.

Tradjenta. Highlights of Prescribing Information (Revised Sep. 2012).

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.

Tribulova, N. et al. "Chronic Disturbances in NO Production Results in Histochemical and Subcellular Alterations of the Rat Heart." Physiol. Res., 2000, vol. 49, No. 1, pp. 77-88.

Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.

Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.

Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.

Charkevich, D. A., Pharmacology, M., Medicina, 1987, pp. 47-48.

\* cited by examiner

8-[3-AMINO-PIPERIDIN-1-YL]-XANTHINES, THEIR PREPARATION AND THEIR USE AS PHARMACEUTICAL COMPOSITIONS

APPLICATION DATA

This application is a continuation of U.S. patent application Ser. No. 11/060,703, filed Feb. 17, 2005, now allowed, and claims the benefit under 35 USC 119(a) of German Application No. 10 2004 008 112, filed Feb. 18, 2004, German Patent Application No. 10 2004 012 921, filed Mar. 17, 2004, and German Patent Application No. 10 2004 032 263, filed Jul. 3, 2004, which applications are incorporated herein by reference in their entirety. This application also claims the benefit under 35 USC 119(e) of U.S. Provisional Application Ser. No. 60/551,108, filed on Mar. 8, 2004, and U.S. Provisional Application Ser. No. 60/562,573, filed on Apr. 15, 2004, which applications are incorporated herein by reference in their entirety.

FIELD OF THE INVENTION

The present invention relates to new substituted xanthines of general formula

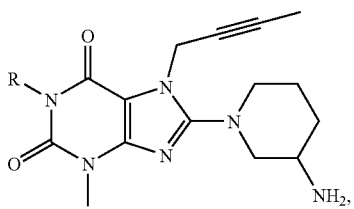

(I)

the tautomers, the enantiomers, the stereoisomers, the mixtures thereof, and the salts thereof, particularly the physiologically acceptable salts thereof, with inorganic or organic acids that have valuable pharmacological properties, particularly an inhibiting effect, on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof, and processes for the preparation thereof.

Xanthine derivatives with an inhibiting effect on DPP-IV are already known from WO 02/068420, WO 02/02560, WO 03/004496, WO 03/024965, WO 04/018468, WO 04/048379, JP 2003300977, and EP 1 338 595, which applications and other applications corresponding thereto are incorporated herein by reference in their entireties.

In the above formula I:
R denotes a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group,
a 2-trifluoromethyl-benzyl, 3-trifluoromethyl-benzyl, or 4-trifluoromethyl-benzyl group,
a 3-trifluoromethoxy-benzyl or 4-trifluoromethoxy-benzyl group,
a 2-cyanobenzyl, 3-cyanobenzyl, or 4-cyanobenzyl group,
a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group,
a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl, or 3,4-dimethoxy-6-fluoro-benzyl group,
a (benzo[1,3]dioxol-5-yl)methyl group,
a [(4-cyano-benzo[1,3]dioxol-5-yl)methyl group,
a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group,
a 2-oxo-2-[2-(pyridin-3-yl)-phenyl]-ethyl or 2-oxo-2-[2-(pyridin-4-yl)-phenyl]-ethyl group,
a (3-cyano-naphthalen-1-yl)methyl, (1,4-dicyano-naphthalen-2-yl)methyl, or (2,4-dimethoxy-naphthalen-1-yl)methyl group,
a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group,
a (pyridin-2-yl)methyl, (6-fluoro-pyridin-2-yl)methyl or (5-methoxy-pyridin-2-yl)methyl group,
a (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group,
a (6-phenyl-pyridin-2-yl)methyl or a ([2,2']bipyridinyl-6-yl)methyl group,
a (pyrimidin-2-yl)methyl, (4-methyl-pyrimidin-2-yl)methyl or (4,6-dimethyl-pyrimidin-2-yl)methyl group,
a (2-phenyl-pyrimidin-4-yl)methyl or (4-phenyl-pyrimidin-2-yl)methyl group,
a [(1-methyl-1H-benzotriazol-5-yl)methyl] group,
a (6-fluoro-quinolin-2-yl)methyl, (7-fluoro-quinolin-2-yl)methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl)methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl)methyl, (6,7-dimethoxy-quinolin-2-yl)methyl, or (8-cyano-quinolin-7-yl)methyl group,
a (1-cyano-isoquinolin-3-yl)methyl, (4-cyano-isoquinolin-1-yl)methyl-(4-cyano-isoquinolin-3-yl)methyl, or [(4-(pyridin-2-yl)-isoquinolin-1-yl]methyl group,
a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl)methyl, (4-cyclopropyl-quinazolin-2-yl)methyl, (2-phenyl-quinazolin-4-yl)methyl, (4-cyano-quinazolin-2-yl)methyl, (4-phenylamino-quinazolin-2-yl)methyl, or (4-benzylamino-quinazolin-2-yl)methyl group,
a (quinoxalin-5-yl)methyl-(quinoxalin-6-yl)methyl or (2,3-dimethyl-quinoxalin-6-yl)methyl group, or
a ([1,5]naphthyridin-3-yl)methyl group,
the tautomers, enantiomers, diastereomers, and the mixtures and the salts thereof.

Preferred are compounds of general formula Ia:

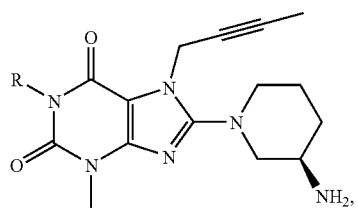

(Ia)

wherein R is as hereinbefore defined, as well as their tautomers and salts.

Also preferred are compounds of general formula Ib

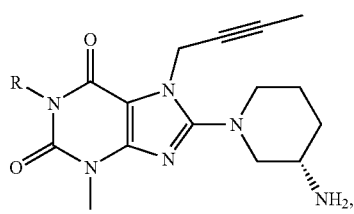

(Ib)

wherein R is as hereinbefore defined, as well as their tautomers and salts.

According to the invention the compounds of general formula I are obtained by methods known, per se, for example, by the following methods:

a) reacting a compound of general formula II

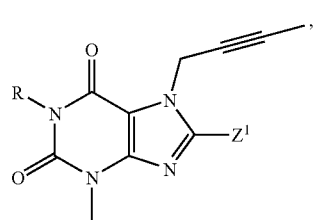

(II)

wherein
R is as hereinbefore defined and
$Z^1$ denotes a leaving group, such as a halogen atom, a substituted hydroxy, mercapto, sulfinyl, sulfonyl or sulfonyloxy group, such as a chlorine or bromine atom, a methanesulfonyl, or methanesulfonyloxy group, with 3-aminopiperidine, the enantiomers or the salts thereof.

The reaction is expediently carried out in a solvent, such as isopropanol, butanol, tetrahydrofuran, dioxane, dimethylformamide, dimethylsulfoxide, ethyleneglycol monomethylether, ethyleneglycol diethylether, or sulfolane, optionally in the presence of an inorganic or tertiary organic base, e.g., sodium carbonate, potassium carbonate, or potassium hydroxide, a tertiary organic base, e.g., triethylamine, or in the presence of N-ethyl-diisopropylamine (Hünig base), while these organic bases may simultaneously also serve as solvent, and optionally in the presence of a reaction accelerator, such as an alkali metal halide or a palladium-based catalyst at temperatures between −20° C. and 180° C., but preferably at temperatures between −10° C. and 120° C. The reaction may, however, also be carried out without solvent or in an excess of the 3-aminopiperidine.

b) deprotecting a compound of general formula III

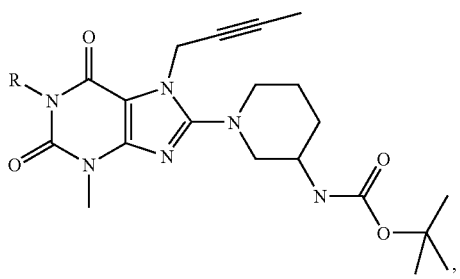

(III)

wherein R is as hereinbefore defined.

The tert.-butyloxycarbonyl group is preferably cleaved by treating with an acid, such as trifluoroacetic acid or hydrochloric acid or by treating with bromotrimethylsilane or iodotrimethylsilane, optionally using a solvent, such as methylene chloride, ethyl acetate, dioxane, methanol, isopropanol, or diethyl ether at temperatures between 0° C. and 80° C.

In the reactions described hereinbefore, any reactive groups present, such as amino, alkylamino, or imino groups, may be protected during the reaction by conventional protecting groups that are cleaved again after the reaction.

For example, a protecting group for an amino, alkylamino, or imino group may be a formyl, acetyl, trifluoroacetyl, ethoxycarbonyl, tert-butoxycarbonyl, benzyloxycarbonyl, benzyl, methoxybenzyl, or 2,4-dimethoxybenzyl group, and additionally, for the amino group, a phthalyl group.

Any protecting group used is optionally, subsequently cleaved, for example, by hydrolysis in an aqueous solvent, e.g., in water, isopropanol/water, acetic acid/water, tetrahydrofuran/water, or dioxane/water, in the presence of an acid, such as trifluoroacetic acid, hydrochloric acid, or sulfuric acid, or in the presence of an alkali metal base, such as sodium hydroxide or potassium hydroxide, or aprotically, e.g., in the presence of iodotrimethylsilane, at temperatures between 0° C. and 120° C., preferably at temperatures between 10° C. and 100° C.

However, a benzyl, methoxybenzyl, or benzyloxycarbonyl group is cleaved, for example, hydrogenolytically, e.g., with hydrogen in the presence of a catalyst, such as palladium/charcoal, in a suitable solvent, such as methanol, ethanol, ethyl acetate, or glacial acetic acid, optionally with the addition of an acid, such as hydrochloric acid, at temperatures between 0° C. and 100° C., but preferably at ambient temperatures between 20° C. and 60° C., and at a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyloxycarbonyl group is preferably cleaved by treating with an acid, such as trifluoroacetic acid or hydrochloric acid, or by treating with iodotrimethylsilane, optionally using a solvent, such as methylene chloride, dioxane, methanol, or diethyl ether.

A trifluoroacetyl group is preferably cleaved by treating with an acid, such as hydrochloric acid, optionally in the presence of a solvent, such as acetic acid, at temperatures between 50° C. and 120° C., or by treating with sodium hydroxide solution, optionally in the presence of a solvent, such as tetrahydrofuran, at temperatures between 0° C. and 50° C.

A phthalyl group is preferably cleaved in the presence of hydrazine or a primary amine, such as methylamine, ethylamine, ethanolamine, or n-butylamine, in a solvent, such as methanol, ethanol, isopropanol, toluene/water, or dioxane, at temperatures between 20° C. and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained that occur as racemates may be separated by methods known, per se, (cf. Allinger N. L. and Eliel E. L. in "Topics in Stereochemistry", Vol. 6, Wiley Interscience, 1971), into their optical enantiomers, and compounds of general formula I with at least 2 asymmetric carbon atoms may be resolved into their diastereomers on the basis of their physical-chemical differences using methods known, per se, e.g., by chromatography and/or fractional crystallisation, and, if these compounds are obtained in racemic form, they may subsequently be resolved into the enantiomers as mentioned above.

The enantiomers are preferably separated by column separation on chiral phases, or by recrystallisation from an optically active solvent, or by reacting with an optically active substance that forms salts or derivatives, such as, e.g., esters or amides with the racemic compound, particularly acids, and the activated derivatives or alcohols thereof, and separating the diastereomeric mixture of salts or derivatives thus obtained, e.g., on the basis of their differences in solubility, whereas the free antipodes may be released from the pure diastereomeric salts or derivatives by the action of suitable agents. Optically active acids in common use are, e.g., the D- and L-forms of tartaric acid, or dibenzoyltartaric acid, di-o-tolyltartaric acid, malic acid, mandelic acid, camphorsulfonic acid, glutamic acid, aspartic acid, or quinic acid. An optically active alcohol may be, for example, (+) or (−)-menthol and an optically active acyl group in amides, for example, may be a (+)- or (−)-menthyloxycarbonyl.

Furthermore, the compounds of formula I obtained may be converted into the salts thereof, particularly, for pharmaceutical use, into the physiologically acceptable salts, with inorganic or organic acids. Acids that may be used for this purpose include, for example, hydrochloric acid, hydrobromic acid, sulfuric acid, methanesulfonic acid, phosphoric acid, fumaric acid, succinic acid, lactic acid, citric acid, tartaric acid, or maleic acid.

The compounds of general formulae II and III used as starting compounds are either known from the literature or may be prepared by methods known from the literature (see Examples I to XXV).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2" that appeared in Proc. Natl. Acad. Sci. Vol. 90, pp. 5757-5761 (1993). The cell extract was obtained from cells solubilized in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 μl of substrate solution (AFC; AFC is amido-4-trifluoromethylcoumarin), final concentration 100 μM, was placed in black microtitre plates. 20 μl of assay buffer (final concentrations 50 mM Tris HCl pH 7.8, 50 mM NaCl, 1% DMSO) was pipetted therein. The reaction was started by the addition of 30 μl of solubilized Caco-2 protein (final concentration 0.14 μg of protein per well). The test substances under investigation were typically added prediluted to 20 μl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example No.) | DPP IV inhibition $IC_{50}$ [nM] |
|---|---|
| 1 | 6 |
| 1(3) | 6 |
| 1(4) | 9 |
| 1(6) | 2 |
| 1(7) | 5 |
| 1(12) | 2 |
| 1(21) | 2 |
| 1(26) | 2 |
| 1(30) | 2 |
| 1(31) | 3 |
| 1(38) | 1 |
| 1(39) | 2 |

The compounds prepared according to the invention are well tolerated, as no toxic side effects could be detected in rats after the oral administration of 10 mg/kg of the compound of Example 1(30), for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, pre-diabetes, reduced glucose tolerance or changes in the fasting blood sugar, diabetic complications (e.g., retinopathy, nephropathy, or neuropathies), metabolic acidosis or ketosis, reactive hypoglycemia, insulin resistance, metabolic syndrome, dyslipidemias of various origins, arthritis, atherosclerosis and related diseases, obesity, allograft transplantation, and osteoporosis caused by calcitonin. In addition, these substances are suitable for preventing B-cell degeneration, such as, e.g., apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides, such as, e.g., GLP-1 and GLP-2 and their link with DPP-IV inhibition, it is expected that the compounds according to the invention will be suitable for achieving, inter a/ia, a sedative or tranquillising effect, as well as having a favorable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases, such as, e.g., irritable bowel syndrome (IBS), Crohn's disease, or ulcerative colitis, and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand, these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as, e.g., rheumatoid arthritis, multiple sclerosis, thyroiditis, and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases, such as Alzheimer's disease, for example. The compounds described may also be used for the treatment of tumors, particularly for modifying tumor invasion and also metastasisation; examples here are their use in treating T-cell lymphomas, acute lymphoblastic leukemia, cell-based pancreatic carcinomas, basal cell carcinomas, or breast cancers. Other indications are stroke, ischemia of various origins, Parkinson's disease, and migraine. In addition, further indications include follicular and epidermal hyperkeratoses, increased keratinocyte proliferation, psoriasis, encephalomyelitis, glomerulonephritis, lipodystrophies, as well as psychosomatic, depressive, and neuropsychiatric diseases of all kinds.

The compounds according to the invention may also be used in conjunction with other active substances. Suitable therapeutic agents for such combinations include, for example, antidiabetic agents, such as metformin, sulfonylureas (e.g., glibenclamid, tolbutamide, glimepiride), nateglinide, repaglinide, thiazolidinediones (e.g., rosiglitazone, pioglitazone), PPAR-gamma agonists (e.g., GI 262570) and antagonists, PPAR-gamma/alpha modulators (e.g., KRP 297), PPAR-gamma/alpha/delta modulators, AMPK activators, ACC1 and ACC2 inhibitors, DGAT inhibitors, SMT3 receptor agonists, 11β-HSD inhibitors, FGF19 agonists or mimetics, alpha-glucosidase inhibitors (e.g., acarbose, voglibose), other DPP-IV inhibitors, alpha2 antagonists, insulin and insulin analogues, GLP-1 and GLP-1 analogues (e.g., exendin-4), or amylin. Also, combinations with SGLT2 inhibitors, such as T-1095 or KGT-1251 (869682), inhibitors of protein tyrosine phosphatase 1, substances which influence deregulated glucose production in the liver, such as, e.g., inhibitors of glucose-6-phosphatase, or fructose-1,6-bisphosphatase, glycogen phosphorylase, glucagon receptor antagonists and inhibitors of phosphoenol—pyruvate carboxykinase, glycogen synthase kinase or pyruvate dehydrokinase, lipid lowering agents, such as HMG-CoA-reductase inhibitors (e.g., simvastatin, atorvastatin), fibrates (e.g., bezafibrate, fenofibrate), nicotinic acid and its derivatives, PPAR-alpha agonists, PPAR-delta agonists, ACAT inhibitors (e.g., avasimibe), or cholesterol absorption inhibitors, such as, for example, ezetimibe, bile acid-binding substances, such as, for example, cholestyramine, inhibitors of ileac bile acid transport, HDL-raising compounds, such as, for example, inhibitors of CETP, or regulators of ABC1 or LXRalpha antagonists, LXRbeta agonists or LXRalpha/beta regulators, or active substances for the treatment of obesity, such as e.g., sibutramine or tetrahydrolipostatin, dexfenfluramine, axokine, antagonists of the cannabinoid1 receptor, MCH-1 receptor antagonists, MC4 receptor agonists, NPY5 or NPY2 antagonists, or $β_3$-agonists, such as SB-418790 or AD-9677, as well as agonists of the 5HT2c receptor.

It is also possible to combine the compounds with drugs for treating high blood pressure, such as, e.g., all antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances, such as hard fat or suitable mixtures thereof, into conventional galenic preparations, such as plain or coated tablets, capsules, powders, suspensions, or suppositories.

The Examples that follow are intended to illustrate the invention:

Preparation of the Starting Compounds

EXAMPLE I

1-[(4-phenylamino-quinazolin-2-yl)methyl]-3-methyl-7-(2-butyn-1-yl)-8-[3-(tert.-butyloxycarbonylamino)-piperidin-1-yl]-xanthine A mixture of 416 mg 3-methyl-7-(2-butyn-1-yl)-8-[3-(tert.-butyloxycarbonylamino)-piperidin-1-yl]-xanthine and 456 mg cesium carbonate in 4 ml N,N-dimethylformamide is stirred for 10 minutes at 80° C., then 324 mg 2-chloromethyl-4-phenylamino-quinazoline are added and the reaction mixture is stirred for two hours at 80° C. Then another 50 mg cesium carbonate and 50 mg chloromethyl-4-phenylamino-quinazoline are added and the mixture is stirred for a further 1.5 hours at 80° C. Then the solvent is distilled off and the residue is distributed between water and ethyl acetate. The organic phase is washed with dilute citric acid, water and saturated sodium chloride solution, dried over magnesium sulfate and evaporated down. The crude product is purified by chromatography over a silica gel column with ethyl acetate/petroleum ether (8:2 to 10:0) as eluant.

Yield: 425 mg (65% of theory)
$R_f$ value: 0.33 (silica gel, ethyl acetate)
Mass spectrum (ESI$^+$): m/z=650 [M+H]$^+$ The following compounds are obtained analogously to Example I:

(1) 1-[(4-benzylamino-quinazolin-2-yl)methyl]-3-methyl-7-(2-butyn-1-yl)-8-[3-(tert.-butyloxycarbonylamino)-piperidin-1-yl]-xanthine $R_f$ value: 0.20 (silica gel, ethyl acetate)
Mass spectrum (ESI$^+$): m/z=664 [M+H]$^+$ (2) 1-[(2-methyl-quinolin-4-yl)methyl]-3-methyl-7-(2-butyn-1-yl)-8-[(R)-3-(tert.-butyloxycarbonylamino)-piperidin-1-yl]-xanthine $R_f$ value: 0.80 (silica gel, methylene chloride/methanol=9:1)
Mass spectrum (ESI$^+$): m/z=572 [M+H]$^+$ (3) 1-[(3-cyano-naphthalen-1-yl)methyl]-3-methyl-7-(2-butyn-1-yl)-8-[(R)-3-(tert.-butyloxycarbonylamino)-piperidin-1-yl]-xanthine $R_f$ value: 0.67 (silica gel, methylene chloride/methanol=95:5)
Mass spectrum (ESI$^+$): m/z=582 [M+H]$^+$ (4) 1-[(2-phenyl-quinazolin-4-yl)methyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)
Mass spectrum (ESI$^+$): m/z=635 [M+H]$^+$ (5) 1-[(4-cyano-isoquinolin-1-yl)methyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/methanol/conc. aqueous ammonia=90:10:1)
Mass spectrum (ESI$^+$): m/z=583 [M+H]$^+$ (6) 1-[(4-cyano-quinolin-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=583 [M+H]$^+$ (7) 1-[2-(3-cyclopropyloxy-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)
Mass spectrum (ESI$^+$): m/z=591 [M+H]$^+$ (8) 1-[2-(3-cyclopropylmethoxy-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.65 (silica gel, methylene chloride/ethyl acetate=1:1)
Mass spectrum (ESI$^+$): m/z=605 [M+H]$^+$ (9) 1-[2-(3-cyclobutyloxy-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.85 (silica gel, methylene chloride/ethyl acetate=1:1)
Mass spectrum (ESI$^+$): m/z=605 [M+H]$^+$

(10) 1-[(1-cyano-isoquinolin-3-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=583 [M+H]$^+$

(11) 1-[(2,4-methoxy-naphthalen-1-yl)methyl]-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)
Mass spectrum (ESI$^+$): m/z=617 [M+H]$^+$

(12) 1-[(2,3-dimethyl-quinoxalin-6-yl)methyl]-3-methyl-7-(2-butyn-1-yl)-8-[(R)-3-(tert.-butyloxycarbonylamino)-piperidin-1-yl]-xanthine $R_f$ value: 0.50 (silica gel, ethyl acetate)
Mass spectrum (ESI$^+$): m/z=587 [M+H]$^+$

(13) 1-[(6-nitro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.45 (silica gel, ethyl acetate/petroleum ether=7:3)
Mass spectrum (ESI$^+$): m/z=603 [M+H]$^+$

(14) 1-[(quinoxalin-5-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=559 [M+H]$^+$

(15) 1-[(6-methoxy-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.65 (silica gel, ethyl acetate)
Mass spectrum (ESI$^+$): m/z=588 [M+H]$^+$

(16) 1-[(6-phenyl-pyridin-2-yl)methyl]-3-methyl-7-(2-butyn-1-yl)-8-[(R)-3-(tert.-butyloxycarbonylamino)-piperidin-1-yl]-xanthine $R_f$ value: 0.43 (silica gel, methylene chloride/methanol=96:4)
Mass spectrum (ESI$^+$): m/z=584 [M+H]$^+$

(17) 1-{[(4-(pyridin-2-yl)-isoquinolin-1-yl]methyl}-3-methyl-7-(2-butyn-1-yl)-8-[(R)-3-(tert.-butyloxycarbonylamino)-piperidin-1-yl]-xanthine

(18) 1-[(7-fluoro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.24 (silica gel, ethyl acetate/petroleum ether=1:1)
Mass spectrum (ESI$^+$): m/z=576 [M+H]$^+$

(19) 1-[(8-nitro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.63 (silica gel, methylene chloride/methanol=95:5)
Mass spectrum (ESI⁺): m/z=603 [M+H]⁺

(20) 1-[(6-fluoro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.47 (silica gel, methylene chloride/methanol=95:5)
Mass spectrum (ESI⁺): m/z=576 [M+H]⁺

(21) 1-[2-oxo-2-(2-bromo-phenyl)-ethyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)
Mass spectrum (ESI⁺): m/z=613, 615 [M+H]⁺

(22) 1-cyanomethyl-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)
Mass spectrum (ESI⁺): m/z=456 [M+H]⁺

(23) 1-[(4-methoxy-quinolin-2-yl)methyl]-3-methyl-7-(2-butyn-1-yl)-8-[(R)-3-(tert.-butyloxycarbonylamino)-piperidin-1-yl]-xanthine Mass spectrum (ESI⁺): m/z=588 [M+H]⁺

(24) 1-[(2-phenyl-pyrimidin-4-yl)methyl]-3-methyl-7-(2-butyn-1-yl)-8-[(R)-3-(tert.-butyloxycarbonylamino)-piperidin-1-yl]-xanthine $R_f$ value: 0.39 (silica gel, methylene chloride/methanol=96:4)
Mass spectrum (ESI⁺): m/z=585 [M+H]⁺

(25) 1-[([1,5]naphthyridin-3-yl)methyl]-3-methyl-7-(2-butyn-1-yl)-8-[(R)-3-(tert.-butyloxycarbonylamino)-piperidin-1-yl]-xanthine $R_f$ value: 0.28 (silica gel, ethyl acetate)
Mass spectrum (ESI⁺): m/z=559 [M+H]⁺

(26) 1-[(3-cyano-4-methyl-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)
Mass spectrum (ESI⁺): m/z=597 [M+H]⁺

(27) 1-[(4,5-dimethyl-quinazolin-2-yl)methyl]-3-methyl-7-(2-butyn-1-yl)-8-[(R)-3-(tert.-butyloxycarbonylamino)-piperidin-1-yl]-xanthine Mass spectrum (ESI⁺): m/z=587 [M+H]⁺

(28) 1-[(5-cyano-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.42 (silica gel, petroleum ether/ethyl acetate=1:2)
Mass spectrum (ESI⁺): m/z=583 [M+H]⁺

(29) 1-[(3-cyano-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.80 (silica gel, methylene chloride/ethyl acetate=1:1)

(30) 1-[(4-phenyl-pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.46 (silica gel, ethyl acetate)

(31) 1-[2-(2-nitro-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.75 (silica gel, ethyl acetate)
Mass spectrum (ESI⁺): m/z=580 [M+H]⁺

(32) 1-[(1,4-dicyano-naphthalen-2-yl)methyl]-3-methyl-7-(2-butyn-1-yl)-8-[(R)-3-(tert.-butyloxycarbonylamino)-piperidin-1-yl]-xanthine $R_f$ value: 0.54 (silica gel, methylene chloride/methanol=95:5)
Mass spectrum (ESI⁺): m/z=607 [M+H]⁺

(33) 1-[(6,7-dimethoxy-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.36 (silica gel, ethyl acetate)
Mass spectrum (ESI⁺): m/z=618 [M+H]⁺

(34) 1-[(quinazolin-6-yl)methyl]-3-methyl-7-(2-butyn-1-yl)-8-[(R)-3-(tert.-butyloxycarbonylamino)-piperidin-1-yl]-xanthine $R_f$ value: 0.20 (silica gel, ethyl acetate)
Mass spectrum (ESI⁺): m/z=559 [M+H]⁺

(35) 1-[(4-cyano-quinazolin-2-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, methylene chloride/ethyl acetate=7:3)
Mass spectrum (ESI⁺): m/z=584 [M+H]⁺

(36) 1-[(quinazolin-7-yl)methyl]-3-methyl-7-(2-butyn-1-yl)-8-[(R)-3-(tert.-butyloxycarbonylamino)-piperidin-1-yl]-xanthine $R_f$ value: 0.20 (silica gel, ethyl acetate)
Mass spectrum (ESI⁺): m/z=559 [M+H]⁺

(37) 1-(2-cyano-benzyl)-3-methyl-7-(2-butyn-1-yl)-8-[(R)-3-(tert.-butyloxycarbonylamino)-piperidin-1-yl]-xanthine $R_f$ value: 0.50 (silica gel, methylene chloride/ethyl acetate=7:3)
Mass spectrum (ESI⁺): m/z=532 [M+H]⁺

(38) 1-(3-cyano-benzyl)-3-methyl-7-(2-butyn-1-yl)-
8-[(R)-3-(tert.-butyloxycarbonylamino)-piperidin-1-
yl]-xanthine R$_f$ value: 0.58 (silica gel, methylene chloride/ethyl acetate=1:1)
Mass spectrum (ESI$^+$): m/z=532 [M+H]$^+$

(39) 1-(4-cyano-benzyl)-3-methyl-7-(2-butyn-1-yl)-
8-[(R)-3-(tert.-butyloxycarbonylamino)-piperidin-1-
yl]-xanthine R$_f$ value: 0.61 (silica gel, methylene chloride/ethyl acetate=1:1)
Mass spectrum (ESI$^+$): m/z=532 [M+H]$^+$

(40) 1-[(pyridin-2-yl)methyl]-3-methyl-7-(2-butyn-
1-yl)-8-[(R)-3-(tert.-butyloxycarbonylamino)-piperi-
din-1-yl]-xanthine Mass spectrum (ESI$^+$): m/z=508 [M+H]$^+$

(41) 1-benzyl-3-methyl-7-(2-butyn-1-yl)-8-[(R)-3-
(tert.-butyloxycarbonylamino)-piperidin-1-yl]-xan-
thine R$_f$ value: 0.70 (silica gel, methylene chloride/ethyl acetate=1:1)
Mass spectrum (ESI$^+$): m/z=507 [M+H]$^+$

(42) 1-(4-methoxy-benzyl)-3-methyl-7-(2-butyn-1-
yl)-8-[(R)-3-(tert.-butyloxycarbonylamino)-piperi-
din-1-yl]-xanthine R$_f$ value: 0.75 (silica gel, ethyl acetate)
Mass spectrum (ESI$^+$): m/z=537 [M+H]$^+$

(43) 1-(2-chloro-benzyl)-3-methyl-7-(2-butyn-1-yl)-
8-[(R)-3-(tert.-butyloxycarbonylamino)-piperidin-1-
yl]-xanthine R$_f$ value: 0.80 (silica gel, ethyl acetate)
Mass spectrum (ESI$^+$): m/z=541, 543 [M+H]$^+$

(44) 1-(2,6-dicyano-benzyl)-3-methyl-7-(2-butyn-1-
yl)-8-[(R)-3-(tert.-butyloxycarbonylamino)-piperi-
din-1-yl]-xanthine Mass spectrum (ESI$^+$): m/z=557 [M+H]$^+$

(45) 1-(2-cyano-4-bromo-benzyl)-3-methyl-7-(2-
butyn-1-yl)-8-[(R)-3-(tert.-butyloxycarbonylamino)-
piperidin-1-yl]-xanthine Mass spectrum (ESI$^+$): m/z=610, 612 [M+H]$^+$

(46) 1-(3-fluoro-benzyl)-3-methyl-7-(2-butyn-1-yl)-
8-[(R)-3-(tert.-butyloxycarbonylamino)-piperidin-1-
yl]-xanthine R$_f$ value: 0.80 (silica gel, ethyl acetate)
Mass spectrum (ESI$^+$): m/z=525 [M+H]$^+$

(47) 1-(3,5-dimethoxy-benzyl)-3-methyl-7-(2-butyn-
1-yl)-8-[(R)-3-(tert.-butyloxycarbonylamino)-piperi-
din-1-yl]-xanthine R$_f$ value: 0.70 (silica gel, ethyl acetate)
Mass spectrum (ESI$^+$): m/z=567 [M+H]$^+$

(48) 1-(2-fluoro-benzyl)-3-methyl-7-(2-butyn-1-yl)-
8-[(R)-3-(tert.-butyloxycarbonylamino)-piperidin-1-
yl]-xanthine R$_f$ value: 0.85 (silica gel, ethyl acetate)
Mass spectrum (ESI$^+$): m/z=525 [M+H]$^+$

(49) 1-[(6-cyano-pyridin-2-yl)methyl]-3-methyl-7-
(2-butyn-1-yl)-8-[(R)-3-(tert.-butyloxycarbony-
lamino)-piperidin-1-yl]-xanthine R$_f$ value: 0.60 (silica gel, methylene chloride/ethyl acetate=1:1)
Mass spectrum (ESI$^+$): m/z=533 [M+H]$^+$

(50) 1-[(3-cyano-pyridin-2-yl)methyl]-3-methyl-7-
(2-butyn-1-yl)-8-[(R)-3-(tert.-butyloxycarbony-
lamino)-piperidin-1-yl]-xanthine R$_f$ value: 0.60 (silica gel, methylene chloride/ethyl acetate=1:1)
Mass spectrum (ESI$^+$): m/z=533 [M+H]$^+$

(51) 1-(2-cyano-3-chloro-benzyl)-3-methyl-7-(2-
butyn-1-yl)-8-[(R)-3-(tert.-butyloxycarbonylamino)-
piperidin-1-yl]-xanthine Mass spectrum (ESI$^+$): m/z=566, 568 [M+H]$^+$

(52) 1-(4-fluoro-benzyl)-3-methyl-7-(2-butyn-1-yl)-
8-[(R)-3-(tert.-butyloxycarbonylamino)-piperidin-1-
yl]-xanthine R$_f$ value: 0.80 (silica gel, ethyl acetate)
Mass spectrum (ESI$^+$): m/z=525 [M+H]$^+$

(53) 1-(4-chloro-benzyl)-3-methyl-7-(2-butyn-1-yl)-
8-[(R)-3-(tert.-butyloxycarbonylamino)-piperidin-1-
yl]-xanthine R$_f$ value: 0.80 (silica gel, ethyl acetate)
Mass spectrum (ESI$^+$): m/z=541, 543 [M+H]$^+$

(54) 1-(2-cyano-4-fluoro-benzyl)-3-methyl-7-(2-
butyn-1-yl)-8-[(R)-3-(tert.-butyloxycarbonylamino)-
piperidin-1-yl]-xanthine Mass spectrum (ESI$^+$): m/z=550 [M+H]$^+$

(55) 1-(3-cyano-4-fluoro-benzyl)-3-methyl-7-(2-
butyn-1-yl)-8-[(R)-3-(tert.-butyloxycarbonylamino)-
piperidin-1-yl]-xanthine Mass spectrum (ESI$^+$): m/z=550 [M+H]$^+$

(56) 1-(2-chloro-4-cyano-benzyl)-3-methyl-7-(2-
butyn-1-yl)-8-[(R)-3-(tert.-butyloxycarbonylamino)-
piperidin-1-yl]-xanthine Mass spectrum (ESI$^+$): m/z=566, 568 [M+H]$^+$

(57) 1-[(5-methoxycarbonyl-furan-2-yl)methyl]-3-methyl-7-(2-butyn-1-yl)-8-[(R)-3-(tert.-butyloxycarbonylamino)-piperidin-1-yl]-xanthine Mass spectrum (ESI⁺): m/z=555 [M+H]⁺

(58) 1-(2-trifluoromethyl-4-cyano-benzyl)-3-methyl-7-(2-butyn-1-yl)-8-[(R)-3-(tert.-butyloxycarbonylamino)-piperidin-1-yl]-xanthine Mass spectrum (ESI⁺): m/z=600 [M+H]⁺

(59) 1-(3,5-dicyano-benzyl)-3-methyl-7-(2-butyn-1-yl)-8-[(R)-3-(tert.-butyloxycarbonylamino)-piperidin-1-yl]-xanthine Mass spectrum (ESI⁺): m/z=557 [M+H]⁺

(60) 1-(3-nitro-4-cyano-benzyl)-3-methyl-7-(2-butyn-1-yl)-8-[(R)-3-(tert.-butyloxycarbonylamino)-piperidin-1-yl]-xanthine Mass spectrum (ESI⁺): m/z=577 [M+H]⁺

(61) 1-[(2-cyano-pyridin-3-yl)methyl]-3-methyl-7-(2-butyn-1-yl)-8-[(R)-3-(tert.-butyloxycarbonylamino)-piperidin-1-yl]-xanthine $R_f$ value: 0.50 (silica gel, methylene chloride/ethyl acetate=1:1)
Mass spectrum (ESI⁺): m/z=533 [M+H]⁺

(62) 1-(2-cyano-4-methoxy-benzyl)-3-methyl-7-(2-butyn-1-yl)-8-[(R)-3-(tert.-butyloxycarbonylamino)-piperidin-1-yl]-xanthine $R_f$ value: 0.70 (silica gel, methylene chloride/ethyl acetate=1:1)
Mass spectrum (ESI⁺): m/z=562 [M+H]⁺

(63) 1-(2-cyano-5-methoxy-benzyl)-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)
Mass spectrum (ESI⁺): m/z=562 [M+H]⁺

(64) 1-(3-methoxy-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)
Mass spectrum (ESI⁺): m/z=537 [M+H]⁺

(65) 1-(3-trifluoromethyl-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)
Mass spectrum (ESI⁺): m/z=575 [M+H]⁺

(66) 1-(3,4-dimethoxy-benzyl)-3-methyl-7-(2-butyn-1-yl)-8-[(R)-3-(tert.-butyloxycarbonylamino)-piperidin-1-yl]-xanthine $R_f$ value: 0.65 (silica gel, ethyl acetate)
Mass spectrum (ESI⁺): m/z=567 [M+H]⁺

(67) 1-(3-chloro-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)
Mass spectrum (ESI⁺): m/z=541, 543 [M+H]⁺

(68) 1-(4-trifluoromethyl-benzyl)-3-methyl-7-(2-butyn-1-yl)-8-[(R)-3-(tert.-butyloxycarbonylamino)-piperidin-1-yl]-xanthine $R_f$ value: 0.85 (silica gel, ethyl acetate)
Mass spectrum (ESI⁺): m/z=575 [M+H]⁺

(69) 1-[([2,2']bipyridinyl-6-yl)methyl]-3-methyl-7-(2-butyn-1-yl)-8-[(R)-3-(tert.-butyloxycarbonylamino)-piperidin-1-yl]-xanthine $R_f$ value: 0.53 (aluminium oxide, methylene chloride/methanol=98:2)
Mass spectrum (ESI⁺): m/z=585 [M+H]⁺

(70) 1-(3,4-dimethoxy-6-fluoro-benzyl)-3-methyl-7-(2-butyn-1-yl)-8-[(R)-3-(tert.-butyloxycarbonylamino)-piperidin-1-yl]-xanthine $R_f$ value: 0.65 (silica gel, ethyl acetate)
Mass spectrum (ESI⁺): m/z=585 [M+H]⁺

(71) 1-[(6-fluoro-pyridin-2-yl)methyl]-3-methyl-7-(2-butyn-1-yl)-8-[(R)-3-(tert.-butyloxycarbonylamino)-piperidin-1-yl]-xanthine Mass spectrum (ESI⁺): m/z=526 [M+H]⁺

(72) 1-[(5-cyano-6-methoxy-pyridin-2-yl)methyl]-3-methyl-7-(2-butyn-1-yl)-8-[(R)-3-(tert.-butyloxycarbonylamino)-piperidin-1-yl]-xanthine Mass spectrum (ESI⁺): m/z=563 [M+H]⁺

(73) 1-(2,6-Difluoro-benzyl)-3-methyl-7-(2-butyn-1-yl)-8-[(R)-3-(tert.-butyloxycarbonylamino)-piperidin-1-yl]-xanthine $R_f$ value: 0.62 (silica gel, ethyl acetate)
Mass spectrum (ESI⁺): m/z=543 [M+H]⁺

(74) 1-(3-trifluoromethoxy-benzyl)-3-methyl-7-(2-butyn-1-yl)-8-[(R)-3-(tert.-butyloxycarbonylamino)-piperidin-1-yl]-xanthine $R_f$ value: 0.67 (silica gel, ethyl acetate)
Mass spectrum (ESI⁺): m/z=591 [M+H]⁺

(75) 1-(4-trifluoromethoxy-benzyl)-3-methyl-7-(2-butyn-1-yl)-8-[(R)-3-(tert.-butyloxycarbonylamino)-piperidin-1-yl]-xanthine $R_f$ value: 0.62 (silica gel, ethyl acetate)
Mass spectrum (ESI$^+$): m/z=591 [M+H]$^+$

(76) 1-[(2-cyano-pyridin-4-yl)methyl]-3-methyl-7-(2-butyn-1-yl)-8-[(R)-3-(tert.-butyloxycarbonylamino)-piperidin-1-yl]-xanthine $R_f$ value: 0.55 (silica gel, methylene chloride/ethyl acetate=1:1)
Mass spectrum (ESI$^+$): m/z=533 [M+H]$^+$

(77) 1-[(5-cyano-pyridin-2-yl)methyl]-3-methyl-7-(2-butyn-1-yl)-8-[(R)-3-(tert.-butyloxycarbonylamino)-piperidin-1-yl]-xanthine $R_f$ value: 0.55 (silica gel, methylene chloride/ethyl acetate=1:1)
Mass spectrum (ESI$^+$): m/z=533 [M+H]$^+$

(78) 1-[(pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.60 (silica gel, ethyl acetate/methanol=9:1)
Mass spectrum (ESI$^+$): m/z=509 [M+H]$^+$

(79) 1-[(4-methyl-pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.60 (silica gel, ethyl acetate/methanol=9:1)
Mass spectrum (ESI$^+$): m/z=523 [M+H]$^+$

(80) 1-[(4,6-dimethyl-pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate/methanol=9:1)
Mass spectrum (ESI$^+$): m/z=537 [M+H]$^+$

(81) 1-[(quinoxalin-6-yl)methyl]-3-methyl-7-(2-butyn-1-yl)-8-bromo-xanthine $R_f$ value: 0.55 (silica gel, ethyl acetate)
Mass spectrum (ESI$^+$): m/z=439, 441 [M+H]$^+$

(82) 1-(3-fluoro-4-methoxy-benzyl)-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)
Mass spectrum (ESI$^+$): m/z=555 [M+H]$^+$

(83) 1-(3,4-difluoro-benzyl)-3-methyl-7-(2-butyn-1-yl)-8-[(R)-3-(tert.-butyloxycarbonylamino)-piperidin-1-yl]-xanthine $R_f$ value: 0.75 (silica gel, ethyl acetate)
Mass spectrum (ESI$^+$): m/z=543 [M+H]$^+$

(84) 1-(2-fluoro-5-methoxy-benzyl)-3-methyl-7-(2-butyn-1-yl)-8-[(R)-3-(tert.-butyloxycarbonylamino)-piperidin-1-yl]-xanthine $R_f$ value: 0.55 (silica gel, ethyl acetate/petroleum ether=3:2)
Mass spectrum (ESI$^+$): m/z=555 [M+H]$^+$

(85) 1-(2-fluoro-3-methoxy-benzyl)-3-methyl-7-(2-butyn-1-yl)-8-[(R)-3-(tert.-butyloxycarbonylamino)-piperidin-1-yl]-xanthine $R_f$ value: 0.48 (silica gel, ethyl acetate/petroleum ether=3:2)
Mass spectrum (ESI$^+$): m/z=555 [M+H]$^+$

(86) 1-[(4-cyano-isoquinolin-3-yl)methyl]-3-methyl-7-(2-butyn-1-yl)-8-[(R)-3-(tert.-butyloxycarbonylamino)-piperidin-1-yl]-xanthine $R_f$ value: 0.55 (silica gel, methylene chloride/methanol=95:5)
Mass spectrum (ESI$^+$): m/z=583 [M+H]$^+$

(87) 1-(2-fluoro-4-methoxy-benzyl)-3-methyl-7-(2-butyn-1-yl)-8-[(R)-3-(tert.-butyloxycarbonylamino)-piperidin-1-yl]-xanthine $R_f$ value: 0.48 (silica gel, ethyl acetate/petroleum ether=1:1)
Mass spectrum (ESI$^+$): m/z=555 [M+H]$^+$

(88) 1-[(furan-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=497 [M+H]$^+$

(89) 1-(3,4-dicyano-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=557 [M+H]$^+$

(90) 1-(4-cyano-2-fluoro-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=550 [M+H]$^+$

(91) (1-(2-cyano-5-fluoro-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=550 [M+H]$^+$

(92) 1-[(5-formyl-furan-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=525 [M+H]$^+$

(93) 1-(2-cyano-6-fluoro-benzyl)-3-methyl-7-(2-butyn-1-yl)-8-[(R)-3-(tert.-butyloxycarbonylamino)-piperidin-1-yl]-xanthine

(94) 1-(4-cyano-3-fluoro-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=550 [M+H]$^+$

(95) 1-(2-cyano-3-methoxy-benzyl)-3-methyl-7-(2-butyn-1-yl)-8-bromo-xanthine $R_f$ value: 0.85 (silica gel, ethyl acetate)
Mass spectrum (ESI$^+$): m/z=442, 444 [M+H]$^+$

(96) 1-[(8-cyano-quinolin-7-yl)methyl]-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)
Mass spectrum (ESI$^+$): m/z=583 [M+H]$^+$

(97) 1-[(4-cyano-pyridin-3-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, ethyl acetate/cyclohexane=3:1)
Mass spectrum (ESI$^+$): m/z=533 [M+H]$^+$

(98) 1-[(8-cyano-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, ethyl acetate/petroleum ether=4:1)
Mass spectrum (ESI$^+$): m/z=583 [M+H]$^+$

(99) 1-[(1-methyl-1H-benzotriazol-5-yl)methyl]-3-methyl-7-(2-butyn-1-yl)-8-[(R)-3-(tert.-butyloxycarbonylamino)-piperidin-1-yl]-xanthine $R_f$ value: 0.30 (silica gel, methylene chloride/ethyl acetate=1:1)
Mass spectrum (ESI$^+$): m/z=562 [M+H]$^+$ (100) 1-[(3-cyano-pyridin-4-yl)methyl]-3-methyl-7-(2-butyn-1-yl)-8-[(R)-3-(tert.-butyloxycarbonylamino)-piperidin-1-yl]-xanthine $R_f$ value: 0.30 (silica gel, methylene chloride/ethyl acetate=1:1)
Mass spectrum (ESI$^+$): m/z=533 [M+H]$^+$ (101) 1-[(3-cyano-pyridin-2-yl)methyl]-3-methyl-7-(2-butyn-1-yl)-8-bromo-xanthine Mass spectrum (ESI$^+$): m/z=413, 415 [M+H]$^+$ (102) 1-[(4-cyano-benzo[1,3]dioxol-5-yl)methyl]-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)
Mass spectrum (ESI$^+$): m/z=576 [M+H]$^+$

EXAMPLE II 3-methyl-7-(2-butyn-1-yl)-8-[(R)-3-(tert.-butyloxycarbonylamino)-piperidin-1-yl]-xanthine 11.00 g of (R)-3-tert.-butyloxycarbonylamino-piperidine are added to 15.00 g of 3-methyl-7-(2-butyn-1-yl)-8-bromo-xanthine and 16.00 g potassium carbonate in 100 ml dimethylsulfoxide and the thick light beige suspension is stirred for four hours with a mechanical stirrer at approx. 114° C. Then another 900 mg of (R)-3-tert.-butyloxycarbonylamino-piperidine, dissolved in 10 ml dimethylsulfoxide, are added to the reaction mixture and this is stirred for a further two hours at 114° C. After cooling to ambient temperature the reaction mixture is liberally diluted with water. The precipitate formed is thoroughly triturated until there are no lumps left and suction filtered. The light-colored solid is again suspended with water, suction filtered, washed with water and diethyl ether and dried in the circulating air dryer at 60° C.
Yield: 19.73 g (94% of theory)
$R_f$ value: 0.64 (silica gel, ethyl acetate)
Mass spectrum (ESI$^+$): m/z=417 [M+H]$^+$ The following compound is obtained analogously to Example II:

(1) 3-methyl-7-(2-butyn-1-yl)-8-[(3-(tert.-butyloxycarbonylamino)-piperidin-1-yl]-xanthine melting point: 235-237° C.
Mass spectrum (ESI$^+$): m/z=417 [M+H]$^+$ (2) 1-[(quinoxalin-6-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, ethyl acetate)
Mass spectrum (ESI$^+$): m/z=559 [M+H]$^+$ (3) 1-[(5-methyl-furan-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=511 [M+H]$^+$ (4) 1-(2-cyano-3-methoxy-benzyl)-3-methyl-7-(2-butyn-1-yl)-8-[(R)-3-(tert.-butyloxycarbonylamino)-piperidin-1-yl]-xanthine $R_f$ value: 0.50 (silica gel, ethyl acetate)
Mass spectrum (ESI$^+$): m/z=562 [M+H]$^+$ (5) 1-[(3-cyano-pyridin-2-yl)methyl]-3-methyl-7-(2-butyn-1-yl)-8-[(S)-3-(tert.-butyloxycarbonylamino)-piperidin-1-yl]-xanthine $R_f$ value: 0.50 (silica gel, ethyl acetate)
Mass spectrum (ESI$^+$): m/z=533 [M+H]$^+$

EXAMPLE III 3-methyl-7-(2-butyn-1-yl)-8-bromo-xanthine 17.06 g 1-bromo-2-butyn are added to 30.17 g of 3-methyl-8-bromo-xanthine and 27.00 ml Hünig base in 370 ml N,N-dimethylformamide. The reaction mixture is stirred for two hours at ambient temperature, then another 1 ml of 1-bromo-2-butyne is added and the mixture is stirred for a further hour at ambient temperature. For working up the reaction mixture is diluted with approx. 300 ml water. The light-colored precipitate formed is suction filtered and washed with water. The filter cake is washed with a little ethanol and diethyl ether and dried at 60° C. in the circulating air dryer.
Yield: 30.50 g (84% of theory)
$R_f$ value: 0.24 (silica gel, methylene chloride/methanol=95:5)
Mass spectrum (ESI$^+$): m/z=297, 299 [M+H]$^+$

EXAMPLE IV

2-chloromethyl-4-phenylamino-quinazoline

Prepared by reacting 500 mg 4-chloro-2-chloromethyl-quinazoline with 438 mg aniline in 12 ml methylene chloride at ambient temperature.

Yield: 518 mg (82% of theory)
$R_f$ value: 0.60 (silica gel, cyclohexane/ethyl acetate=1:1)
Mass spectrum (ESI$^+$): m/z=270, 272 [M+H]$^+$ The following compound is obtained analogously to Example IV:

(1) 2-chloromethyl-4-benzylamino-quinazoline $R_f$ value: 0.60 (silica gel, cyclohexane/ethyl acetate=1:1)
Mass spectrum (ESI$^+$): m/z=284, 286 [M+H]$^+$

EXAMPLE V

1-bromomethyl-4-cyano-isoquinoline

Prepared by bromination of 1-methyl-4-cyano-isoquinoline with N-bromosuccinimide in the presence of azobisisobutyronitrile in carbon tetrachloride at 80° C.

$R_f$ value: 0.51 (silica gel, methylene chloride)
Mass spectrum (EI): m/z=246, 248 [M]$^+$ The following compounds are obtained analogously to Example V:

(1) 2-bromomethyl-4-cyano-quinoline

Mass spectrum (ESI$^+$): m/z=247, 249 [M+H]$^+$ (2) 3-bromomethyl-1-cyano-isoquinoline Mass spectrum (ESI$^+$): m/z=247, 249 [M+H]$^+$ (3) 1-bromomethyl-4-(pyridin-2-yl)-isoquinoline $R_f$ value: 0.47 (silica gel, methylene chloride/methanol=9:1)

(4) 2-bromomethyl-4-methoxy-quinoline

Mass spectrum (ESI$^+$): m/z=252, 254 [M+H]$^+$ (5) 3-bromomethyl-[1,5]naphthyridine Mass spectrum (ESI$^+$): m/z=223, 225 [M+H]$^+$ (6) 2-bromomethyl-5-cyano-quinoline $R_f$ value: 0.28 (silica gel, petroleum ether/ethyl acetate=5:1)
Mass spectrum (ESI$^+$): m/z=247, 249 [M+H]$^+$ (7) 2-bromomethyl-3-cyano-quinoline $R_f$ value: 0.65 (silica gel, cyclohexane/ethyl acetate=3:1)

(8) 2-bromomethyl-4-phenyl-pyrimidine $R_f$ value: 0.88 (silica gel, ethyl acetate)
Mass spectrum (ESI$^+$): m/z=249, 251 [M+H]$^+$ (9) 2-bromomethyl-1,4-dicyano-naphthalene $R_f$ value: 0.48 (silica gel, petroleum ether/ethyl acetate=9:1)
Mass spectrum (EI$^+$): m/z=270, 272 [M]$^+$

(10) 2-bromomethyl-6,7-dimethoxy-quinoline $R_f$ value: 0.70 (silica gel, methylene chloride/methanol=95:5)
Mass spectrum (ESI$^+$): m/z=282, 284 [M+H]$^+$

(11) 2-bromomethyl-4-cyano-quinazoline $R_f$ value: 0.85 (silica gel, methylene chloride/methanol=99:1)
Mass spectrum (EI$^+$): m/z=247, 249 [M]$^+$

(12) 7-bromomethyl-quinazoline $R_f$ value: 0.15 (silica gel, methylene chloride/methanol=99:1)
Mass spectrum (ESI$^+$): m/z=223, 225 [M+H]$^+$

(13) 2-trifluoromethyl-4-cyano-benzylbromide

(14) 2-bromomethyl-5-cyano-6-methoxy-pyridine

Mass spectrum (ESI$^+$): m/z=227, 229 [M+H]$^+$

(15) 3-bromomethyl-4-cyano-isoquinoline $R_f$ value: 0.43 (silica gel, petroleum ether/ethyl acetate=7:3)

(16) 7-bromomethyl-8-cyano-quinoline $R_f$ value: 0.25 (silica gel, petroleum ether/ethyl acetate=7:3)
Mass spectrum (ESI$^+$): m/z=247, 249 [M+H]$^+$

(17) 2-bromomethyl-8-cyano-quinoline $R_f$ value: 0.75 (silica gel, methylene chloride/methanol=99:1)
Mass spectrum (ESI$^+$): m/z=247, 249 [M+H]$^+$

EXAMPLE VI

2-bromo-1-(3-cyclopropyloxy-phenyl)-ethanone

Prepared by bromination of 1-(3-cyclopropyloxy-phenyl)-ethanone with phenyltrimethylammonium tribromide in methylene chloride at reflux temperature.

$R_f$ value: 0.75 (silica gel, cyclohexane/ethyl acetate=3:1)
Mass spectrum (ESI$^+$): m/z=255, 257 [M+H]$^+$ The following compounds are obtained analogously to Example VI:

(1) 2-bromo-1-(3-cyclopropylmethoxy-phenyl)-ethanone $R_f$ value: 0.70 (silica gel, cyclohexane/ethyl acetate=3:1)

(2) 2-bromo-1-(3-cyclobutyloxy-phenyl)-ethanone $R_f$ value: 0.70 (silica gel, cyclohexane/ethyl acetate=3:1)

EXAMPLE VII

1-(3-cyclopropyloxy-phenyl)-ethanone

Prepared by reacting 3-hydroxyacetophenone with bromocyclopropane in the presence of potassium iodide and potassium-tert.butoxide in N,N-dimethylformamide in the microwave at 220° C.

R_f value: 0.65 (silica gel, cyclohexane/ethyl acetate=3:1)
Mass spectrum (ESI$^+$): m/z=177 [M+H]$^+$ The following compounds are obtained analogously to Example VII:

(1) 1-(3-cyclopropylmethoxy-phenyl)-ethanone

R_f value: 0.70 (silica gel, cyclohexane/ethyl acetate=3:1)
Mass spectrum (ESI$^+$): m/z=191 [M+H]$^+$ (2) 1-(3-cyclobutyloxy-phenyl)-ethanone R_f value: 0.65 (silica gel, cyclohexane/ethyl acetate=3:1)
Mass spectrum (ESI$^+$): m/z=191 [M+H]$^+$

EXAMPLE VIII 1-chloromethyl-2,4-dimethoxy-naphthalene

Prepared by chlorinating 1-hydroxymethyl-2,4-dimethoxy-naphthalene with thionyl chloride in methylene chloride at ambient temperature.
R_f value: 0.78 (silica gel, cyclohexane/ethyl acetate=1:1)
Mass spectrum (EI): m/z=236, 238 [M]$^+$

EXAMPLE IX 1-hydroxymethyl-2,4-dimethoxy-naphthalene

Prepared by reducing 2,4-dimethoxy-naphthalene-1-carboxaldehyde with sodium borohydride in a mixture of dioxane and water (3:1) at ambient temperature.
R_f value: 0.48 (silica gel, cyclohexane/ethyl acetate=1:1)

EXAMPLE X

1-[(6-amino-quinolin-2-yl)methyl]-3-methyl-7-(2-butyn-1-yl)-8-[(R)-3-(tert.-butyloxycarbonylamino)-piperidin-1-yl]-xanthine Prepared by treating 1-[(6-nitro-quinolin-2-yl)methyl]-3-methyl-7-(2-butyn-1-yl)-8-[(R)-3-(tert.-butyloxycarbonylamino)-piperidin-1-yl]-xanthine with sodium dithionite in a mixture of ethanol/water (5:2) at 55-60° C.
R_f value: 0.40 (silica gel, methylene chloride/methanol=95:5)
Mass spectrum (ESI$^+$): m/z=573 [M+H]$^+$

EXAMPLE XI 1-methyl-4-(pyridin-2-yl)-isoquinoline

Prepared by reacting 4-bromo-1-methyl-isoquinoline with lithium-triisopropoxy-2-pyridinyl-boronate in the presence of tetrakis(triphenylphosphine)palladium, triphenylphosphine, sodium carbonate, and copper(I)iodide in 1,4-dioxane at reflux temperature.
R_f value: 0.22 (silica gel, methylene chloride/methanol=95:5)
Mass spectrum (ESI$^+$): m/z=221 [M+H]$^+$

EXAMPLE XII

1-[(8-amino-quinolin-2-yl)methyl]-3-methyl-7-(2-butyn-1-yl)-8-[(R)-3-(tert.-butyloxycarbonylamino)-piperidin-1-yl]-xanthine Prepared by treating 1-[(8-nitro-quinolin-2-yl)methyl]-3-methyl-7-(2-butyn-1-yl)-8-[(R)-3-(tert.-butyloxycarbonylamino)-piperidin-1-yl]-xanthine with iron powder in a mixture of glacial acetic acid, ethanol and water (2:20:5) at reflux temperature.
R_f value: 0.50 (silica gel, methylene chloride/methanol=95:5)
Mass spectrum (ESI$^+$): m/z=573 [M+H]$^+$

EXAMPLE XIII

1-{2-oxo-2-[2-(pyridin-3-yl)-phenyl]-ethyl}-3-methyl-7-(2-butyn-1-yl)-8-[(R)-3-(tert.-butyloxycarbonylamino)-piperidin-1-yl]-xanthine Prepared by reacting 1-[2-oxo-2-(2-bromo-phenyl)-ethyl]-3-methyl-7-(2-butyn-1-yl)-8-[(R)-3-(tert.-butyloxycarbonylamino)-piperidin-1-yl]-xanthine with pyridine-3-boric acid in the presence of tetrakis(triphenylphosphine)palladium, tetra-n-butylammonium bromide and sodium carbonate in a mixture of toluene/ethanol (1:1) at 105° C.
R_f value: 0.55 (silica gel, ethyl acetate)
Mass spectrum (ESI$^+$): m/z=612 [M+H]$^+$ The following compound is obtained analogously to Example XII:

(1) 1-{2-oxo-2-[2-(pyridin-4-yl)-phenyl]-ethyl}-3-methyl-7-(2-butyn-1-yl)-8-[(R)-3-(tert.-butyloxycarbonylamino)-piperidin-1-yl]-xanthine (The reaction is carried out with 4-(4,4,5,5-tetramethyl-[1,3,2]dioxaborolan-2-yl)-pyridine).
R_f value: 0.40 (silica gel, ethyl acetate)
Mass spectrum (ESI$^+$): m/z=612 [M+H]$^+$

EXAMPLE XIV

1-[(4-ethyl-quinazolin-2-yl)methyl]-3-methyl-7-(2-butyn-1-yl)-8-[(R)-3-(tert.-butyloxycarbonylamino)-piperidin-1-yl]-xanthine Prepared by treating 1-cyanomethyl-3-methyl-7-(2-butyn-1-yl)-8-[(R)-3-(tert.-butyloxycarbonylamino)-piperidin-1-yl]-xanthine with potassium-tert.-butoxide in methanol and subsequently reacting the resulting iminoester with 2-aminopropiophenone in the presence of glacial acetic acid.
R_f value: 0.60 (silica gel, ethyl acetate)
Mass spectrum (ESI$^+$): m/z=587 [M+H]$^+$ The following compound is obtained analogously to Example XIV:

(1) 1-[(4-cyclopropyl-quinazolin-2-yl)methyl]-3-methyl-7-(2-butyn-1-yl)-8-[(R)-3-(tert.-butyloxycarbonylamino)-piperidin-1-yl]-xanthine R_f value: 0.70 (silica gel, ethyl acetate)
Mass spectrum (ESI$^+$): m/z=599 [M+H]$^+$

EXAMPLE XV 2-chloromethyl-3-cyano-4-methyl-quinoline

Prepared by reacting 3-cyano-2,4-dimethyl-1-oxy-quinoline with benzosulfonic acid chloride in toluene at 80° C.
R_f value: 0.55 (silica gel, cyclohexane/ethyl acetate=2:1)
Mass spectrum (ESI$^+$): m/z=217, 219 [M+H]$^+$

EXAMPLE XVI 3-cyano-2,4-dimethyl-1-oxy-quinoline

Prepared by treating 3-cyano-2,4-dimethyl-quinoline with aqueous hydrogen peroxide solution (35%) in glacial acetic acid at 60° C.

$R_f$ value: 0.35 (silica gel, ethyl acetate)
Mass spectrum (ESI$^+$): m/z=199 [M+H]$^+$

EXAMPLE XVII 2-chloromethyl-4,5-dimethyl-quinazoline

Prepared by reacting 1-(2-amino-6-methyl-phenyl)-ethanone with chloroacetonitrile in dioxane while piping in hydrogen chloride at 30-38° C.
Mass spectrum (ESI$^+$): m/z=207, 209 [M+H]$^+$

EXAMPLE XVIII

1-[(2-methyl-quinazolin-4-yl)methyl]-3-methyl-7-(2-butyn-1-yl)-8-[(R)-3-(tert.-butyloxycarbonylamino)-piperidin-1-yl]-xanthine Prepared by reacting 1-[2-(2-acetylamino-phenyl)-2-oxo-ethyl]-3-methyl-7-(2-butyn-1-yl)-8-[(R)-3-(tert.-butyloxy-carbonylamino)-piperidin-1-yl]-xanthine with ethanolic ammonia (6 M) and ammonium chloride in the autoclave at 150° C.

$R_f$ value: 0.35 (silica gel, ethyl acetate)
Mass spectrum (ESI$^+$): m/z=573 [M+H]$^+$

EXAMPLE XIX

1-[2-(2-acetylamino-phenyl)-2-oxo-ethyl]-3-methyl-7-(2-butyn-1-yl)-8-[(R)-3-(tert.-butyloxycarbony-lamino)-piperidin-1-yl]-xanthine Prepared by reacting 1-[2-(2-amino-phenyl)-2-oxo-ethyl]-3-methyl-7-(2-butyn-1-yl)-8-[(R)-3-(tert.-butyloxycarbony-lamino)-piperidin-1-yl]-xanthine with acetyl chloride in the presence of pyridine in methylene chloride at ambient temperature.

$R_f$ value: 0.79 (silica gel, ethyl acetate)
Mass spectrum (ESI$^+$): m/z=592 [M+H]$^+$

EXAMPLE XX

1-[2-(2-amino-phenyl)-2-oxo-ethyl]-3-methyl-7-(2-butyn-1-yl)-8-[(R)-3-(tert.-butyloxycarbonylamino)-piperidin-1-yl]-xanthine Prepared by reducing 1-[2-(2-nitro-phenyl)-2-oxo-ethyl]-3-methyl-7-(2-butyn-1-yl)-8-[(R)-3-(tert.-butyloxycarbony-lamino)-piperidin-1-yl]-xanthine with tin(II)chloride dihydrate in tetrahydrofuran at ambient temperature.

$R_f$ value: 0.85 (silica gel, ethyl acetate)
Mass spectrum (ESI$^+$): m/z=550 [M+H]$^+$

EXAMPLE XXI

1-[(furan-3-yl)methyl]-3-methyl-7-(2-butyn-1-yl)-8-[(R)-3-(tert.-butyloxycarbonyl-amino)-piperidin-1-yl]-xanthine A mixture of 300 mg of 3-methyl-7-(2-butyn-1-yl)-8-[(R)-3-(tert.-butyloxycarbonyl-amino)-piperidin-1-yl]-xanthine, 95 µl furan-3-yl-methanol, 302 mg triphenylphosphine and 226 µl diisopropyl azodicarboxylate in 4 ml tetrahydrofuran is stirred overnight at ambient temperature. For working up the reaction mixture is combined with saturated potassium carbonate solution and extracted with ethyl acetate. The combined organic phases are dried over magnesium sulfate and evaporated down. The flask residue is chromatographed over a silica gel column with cyclohexane/ethyl acetate (1:1 to 3:7).

Yield: 330 mg (92% of theory)
Mass spectrum (ESI$^+$): m/z=497 [M+H]$^+$

The following compounds are obtained analogously to Example XXI:

(1) 1-[(5-methyl-furan-2-yl)methyl]-3-methyl-7-(2-butyn-1-yl)-8-bromo-xanthine

Mass spectrum (ESI$^+$): m/z=391, 393 [M+H]$^+$ (2) 1-[(5-bromo-furan-2-yl)methyl]-3-methyl-7-(2-butyn-1-yl)-8-[(R)-3-(tert.-butyloxy-carbonylamino)-piperidin-1-yl]-xanthine Mass spectrum (ESI$^+$): m/z=575, 577 [M+H]$^+$

EXAMPLE XXII

1-[(5-cyano-furan-2-yl)methyl]-3-methyl-7-(2-butyn-1-yl)-8-[(R)-3-(tert.-butyloxy-carbonylamino)-piperidin-1-yl]-xanthine Prepared by reacting 1-[(5-formyl-furan-2-yl)methyl]-3-methyl-7-(2-butyn-1-yl)-8-[(R)-3-(tert.-butyloxycarbony-lamino)-piperidin-1-yl]-xanthine with hydroxylamine-O-sulfonic acid and pyridine in toluene at reflux temperature.

EXAMPLE XXIII 5-(methanesulfonyloxymethyl)-2-furan-carboxaldehyde

Prepared by reacting 5-(hydroxymethyl)-2-furan-carboxaldehyde with methanesulfonic acid chloride in the presence of triethylamine in methylene chloride at ambient temperature. The crude product is further reacted without any more purification.

EXAMPLE XXIV 2-chloromethyl-3-cyano-pyridine

Prepared from 2-(hydroxymethyl)-nicotinamide by reaction with thionyl chloride in acetonitrile and subsequent dehydration of the 2-(chloromethyl)-nicotinamide thus obtained with trifluoroacetic acid anhydride in the presence of triethylamine in methylene chloride.

Alternatively the compound is also obtained in one step by refluxing 2-(hydroxy-methyl)-nicotinamide with phosphorus oxychloride.

$R_f$ value: 0.85 (silica gel, methylene chloride/methanol=9:1)
Mass spectrum (ESI$^+$): m/z=153, 155 [M+H]$^+$

EXAMPLE XXV

8-cyano-7-methyl-quinoline

Prepared by reacting 8-bromo-7-methyl-quinoline with zinc cyanide in the presence of tetrakis(triphenylphosphine) palladium in N-methylpyrrolidinone under a protective gas atmosphere at 100-105° C.

$R_f$ value: 0.35 (silica gel, petroleum ether/ethyl acetate=7:3)
Mass spectrum (ESI$^+$): m/z=169 [M+H]$^+$

EXAMPLE XXVI

2-methyl-8-cyano-quinoline

Prepared by reacting 2-methyl-8-bromo-quinoline with copper(I)cyanide in N-methylpyrrolidinone under a protective gas atmosphere at 180° C.

$R_f$ value: 0.40 (silica gel, petroleum ether/ethyl acetate=7:3)
Mass spectrum (ESI$^+$): m/z=169 [M+H]$^+$ Preparation of the Final Compounds

EXAMPLE 1

1-[(4-phenylamino-quinazolin-2-yl)methyl]-3-methyl-7-(2-butyn-1-yl)-8-(3-amino-piperidin-1-yl)-xanthine A mixture of 400 mg 1-[(4-phenylamino-quinazolin-2-yl)methyl]-3-methyl-7-(2-butyn-1-yl)-8-[3-(tert.-butyloxycarbonylamino)-piperidin-1-yl]-xanthine in 10 ml methylene chloride is combined with 2 ml isopropanolic hydrochloric acid (5-6 M) and stirred for three hours at ambient temperature. Then the reaction mixture is diluted with methylene chloride, combined with ice water and made alkaline with 3 M potassium carbonate solution. The aqueous phase is extracted with methylene chloride. The combined extracts are washed with water, dried over magnesium sulfate and evaporated down. The flask residue is stirred with diethyl ether, suction filtered, washed with diethyl ether and dried in vacuo.

Yield: 274 mg (81% of theory)
$R_f$ value: 0.50 (silica gel, methylene chloride/methanol/conc. aqueous ammonia=90:10:0.1)
Mass spectrum (ESI$^+$): m/z=550 [M+H]$^+$ The following compounds are obtained analogously to Example 1:

(1) 1-[(4-benzylamino-quinazolin-2-yl)methyl]-3-methyl-7-(2-butyn-1-yl)-8-(3-amino-piperidin-1-yl)-xanthine $R_f$ value: 0.43 (silica gel, methylene chloride/methanol/conc. aqueous ammonia=90:10:0.1)
Mass spectrum (ESI$^+$): m/z=564 [M+H]$^+$ (2) 1-[(2-methyl-quinolin-4-yl)methyl]-3-methyl-7-(2-butyn-1-yl)-8-((R)-3-amino-piperidin-1-yl)-xanthine Mass spectrum (ESI$^+$): m/z=472 [M+H]$^+$ (3) 1-[(3-cyano-naphthalen-1-yl)methyl]-3-methyl-7-(2-butyn-1-yl)-8-((R)-3-amino-piperidin-1-yl)-xanthine $R_f$ value: 0.55 (silica gel, methylene chloride/methanol/conc. aqueous ammonia=90:10:1)
Mass spectrum (ESI$^+$): m/z=482 [M+H]$^+$ (4) 1-[(2-phenyl-quinazolin-4-yl)methyl]-3-methyl-7-(2-butyn-1-yl)-8-((R)-3-amino-piperidin-1-yl)-xanthine $R_f$ value: 0.45 (reversed phase ready-made TLC plate (E. Merck), acetonitrile/water/trifluoroacetic acid=50:50:1)
Mass spectrum (ESI$^+$): m/z=535 [M+H]$^+$ (5) 1-[(4-cyano-isoquinolin-1-yl)methyl]-3-methyl-7-(2-butyn-1-yl)-8-((R)-3-amino-piperidin-1-yl)-xanthine $R_f$ value: 0.15 (silica gel, methylene chloride/methanol/conc. aqueous ammonia=90:10:1)
Mass spectrum (ESI$^+$): m/z=483 [M+H]$^+$ (6) 1-[(4-cyano-quinolin-2-yl)methyl]-3-methyl-7-(2-butyn-1-yl)-8-((R)-3-amino-piperidin-1-yl)-xanthine Mass spectrum (ESI$^+$): m/z=483 [M+H]$^+$ (7) 1-[2-(3-cyclopropyloxy-phenyl)-2-oxo-ethyl]-3-methyl-7-(2-butyn-1-yl)-8-((R)-3-amino-piperidin-1-yl)-xanthine $R_f$ value: 0.45 (reversed phase ready-made TLC plate (E. Merck), acetonitrile/water/trifluoroacetic acid=50:50:1)
Mass spectrum (ESI$^+$): m/z=491 [M+H]$^+$ (8) 1-[2-(3-cyclopropylmethoxy-phenyl)-2-oxo-ethyl]-3-methyl-7-(2-butyn-1-yl)-8-((R)-3-amino-piperidin-1-yl)-xanthine $R_f$ value: 0.35 (reversed phase ready-made TLC plate (E. Merck), acetonitrile/water/trifluoroacetic acid=50:50:1)
Mass spectrum (ESI$^+$): m/z=505 [M+H]$^+$ (9) 1-[2-(3-cyclobutyloxy-phenyl)-2-oxo-ethyl]-3-methyl-7-(2-butyn-1-yl)-8-((R)-3-amino-piperidin-1-yl)-xanthine $R_f$ value: 0.40 (reversed phase ready-made TLC plate (E. Merck), acetonitrile/water/trifluoroacetic acid=50:50:1)
Mass spectrum (ESI$^+$): m/z=505 [M+H]$^+$

(10) 1-[(1-cyano-isoquinolin-3-yl)methyl]-3-methyl-7-(2-butyn-1-yl)-8-((R)-3-amino-piperidin-1-yl)-xanthine Mass spectrum (ESI$^+$): m/z=483 [M+H]$^+$

(11) 1-[(2,4-methoxy-naphthalen-1-yl)methyl]-3-methyl-7-(2-butyn-1-yl)-8-((R)-3-amino-piperidin-1-yl)-xanthine $R_f$ value: 0.55 (silica gel, methylene chloride/methanol/conc. aqueous ammonia=90:10:0.1)
Mass spectrum (ESI$^+$): m/z=517 [M+H]$^+$

(12) 1-[(2,3-dimethyl-quinoxalin-6-yl)methyl]-3-methyl-7-(2-butyn-1-yl)-8-((R)-3-amino-piperidin-1-yl)-xanthine $R_f$ value: 0.48 (silica gel, methylene chloride/methanol/conc. aqueous ammonia=90:10:0.1)
Mass spectrum (ESI$^+$): m/z=487 [M+H]$^+$

(13) 1-[(6-amino-quinolin-2-yl)methyl]-3-methyl-7-(2-butyn-1-yl)-8-((R)-3-amino-piperidin-1-yl)-xanthine $R_f$ value: 0.40 (silica gel, methylene chloride/methanol/conc. aqueous ammonia=90:10:0.1)
Mass spectrum (ESI$^+$): m/z=473 [M+H]$^+$

(14) 1-[(quinoxalin-5-yl)methyl]-3-methyl-7-(2-butyn-1-yl)-8-((R)-3-amino-piperidin-1-yl)-xanthine-hydrochloride Mass spectrum (ESI$^+$): m/z=459 [M+H]$^+$

(15) 1-[(6-methoxy-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)
Mass spectrum (ESI$^+$): m/z=488 [M+H]$^+$

(16) 1-[(6-phenyl-pyridin-2-yl)methyl]-3-methyl-7-(2-butyn-1-yl)-8-((R)-3-amino-piperidin-1-yl)-xanthine $R_f$ value: 0.37 (silica gel, methylene chloride/methanol/conc. aqueous ammonia=90:10:1)
Mass spectrum (ESI$^+$): m/z=484 [M+H]$^+$

(17) 1-{[(4-(pyridin-2-yl)-isoquinolin-1-yl]methyl}-3-methyl-7-(2-butyn-1-yl)-8-((R)-3-amino-piperidin-1-yl)-xanthine $R_f$ value: 0.37 (silica gel, methylene chloride/methanol/conc. aqueous ammonia=80:20:1)
Mass spectrum (ESI$^+$): m/z=535 [M+H]$^+$

(18) 1-[(7-fluoro-quinolin-2-yl)methyl]-3-methyl-7-(2-butyn-1-yl)-8-((R)-3-amino-piperidin-1-yl)-xanthine $R_f$ value: 0.58 (silica gel, methylene chloride/methanol/conc. aqueous ammonia=90:10:1)
Mass spectrum (ESI$^+$): m/z=476 [M+H]$^+$

(19) 1-[(8-amino-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)
Mass spectrum (ESI$^+$): m/z=473 [M+H]$^+$

(20) 1-[(6-fluoro-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)
Mass spectrum (ESI$^+$): m/z=476 [M+H]$^+$

(21) 1-{2-oxo-2-[2-(pyridin-3-yl)-phenyl]-ethyl}-3-methyl-7-(2-butyn-1-yl)-8-((R)-3-amino-piperidin-1-yl)-xanthine $R_f$ value: 0.55 (reversed phase ready-made TLC plate (E. Merck), acetonitrile/water/trifluoroacetic acid=50:50:1)
Mass spectrum (ESI$^+$): m/z=512 [M+H]$^+$

(22) 1-[(4-ethyl-quinazolin-2-yl)methyl]-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:0.1)
Mass spectrum (ESI$^+$): m/z=487 [M+H]$^+$

(23) 1-[(4-cyclopropyl-quinazolin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=499 [M+H]$^+$

(24) 1-[(4-methoxy-quinolin-2-yl)methyl]-3-methyl-7-(2-butyn-1-yl)-8-((R)-3-amino-piperidin-1-yl)-xanthine Mass spectrum (ESI$^+$): m/z=488 [M+H]$^+$

(25) 1-[(2-phenyl-pyrimidin-4-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)
Mass spectrum (ESI$^+$): m/z=485 [M+H]$^+$

(26) 1-[([1,5]naphthyridin-3-yl)methyl]-3-methyl-7-(2-butyn-1-yl)-8-((R)-3-amino-piperidin-1-yl)-xanthine $R_f$ value: 0.52 (silica gel, methylene chloride/methanol/conc. aqueous ammonia=90:10:1)
Mass spectrum (ESI$^+$): m/z=459 [M+H]$^+$

(27) 1-[(3-cyano-4-methyl-quinolin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.50 (reversed phase ready-made TLC plate (E. Merck), acetonitrile/water/trifluoroacetic acid=50:50:1)
Mass spectrum (ESI$^+$): m/z=497 [M+H]$^+$

(28) 1-[(4,5-dimethyl-quinazolin-2-yl)methyl]-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=487 [M+H]$^+$

(29) 1-[(5-cyano-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)
Mass spectrum (ESI$^+$): m/z=483 [M+H]$^+$

(30) 1-[(3-cyano-quinolin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.50 (reversed phase ready-made TLC plate (E. Merck), acetonitrile/water/trifluoroacetic acid=50:50:1)
Mass spectrum (ESI$^+$): m/z=483 [M+H]$^+$

(31) 1-[(4-phenyl-pyrimidin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)
Mass spectrum (ESI$^+$): m/z=485 [M+H]$^+$

(32) 1-[(2-methyl-quinazolin-4-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.38 (silica gel, methylene chloride/methanol/conc. aqueous ammonia=90:10:1)
Mass spectrum (ESI$^+$): m/z=473 [M+H]$^+$

(33) 1-[(1,4-dicyano-naphthalen-2-yl)methyl]-3-methyl-7-(2-butyn-1-yl)-8-((R)-3-amino-piperidin-1-yl)-xanthine-hydrochloride $R_f$ value: 0.86 (silica gel, methylene chloride/methanol/conc. aqueous ammonia=90:10:1)
Mass spectrum (ESI$^+$): m/z=507 [M+H]$^+$

(34) 1-{2-oxo-2-[2-(pyridin-4-yl)-phenyl]-ethyl}-3-methyl-7-(2-butyn-1-yl)-8-((R)-3-amino-piperidin-1-yl)-xanthine (BOC cleaving carried out with trifluoroacetic acid)
$R_f$ value: 0.55 (reversed phase ready-made TLC plate (E. Merck), acetonitrile/water/trifluoroacetic acid=50:50:1)
Mass spectrum (ESI$^+$): m/z=512 [M+H]$^+$

(35) 1-[(6,7-dimethoxy-quinolin-2-yl)methyl]-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:1)
Mass spectrum (ESI$^+$): m/z=518 [M+H]$^+$

(36) 1-[(quinazolin-6-yl)methyl]-3-methyl-7-(2-butyn-1-yl)-8-((R)-3-amino-piperidin-1-yl)-xanthine-hydrochloride $R_f$ value: 0.50 (silica gel, methylene chloride/methanol/conc. aqueous ammonia=90:10:0.1)
Mass spectrum (ESI$^+$): m/z=459 [M+H]$^+$

(37) 1-[(4-cyano-quinazolin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.50 (silica gel, methylene chloride/methanol/conc. aqueous ammonia=90:10:1)
Mass spectrum (ESI$^+$): m/z=484 [M+H]$^+$

(38) 1-[(quinazolin-7-yl)methyl]-3-methyl-7-(2-butyn-1-yl)-8-((R)-3-amino-piperidin-1-yl)-xanthine $R_f$ value: 0.43 (silica gel, methylene chloride/methanol/conc. aqueous ammonia=90:10:0.1)
Mass spectrum (ESI$^+$): m/z=459 [M+H]$^+$

(39) 1-(2-cyano-benzyl)-3-methyl-7-(2-butyn-1-yl)-8-((R)-3-amino-piperidin-1-yl)-xanthine (BOC cleaving carried out with trifluoroacetic acid)
$R_f$ value: 0.35 (silica gel, methylene chloride/methanol/conc. aqueous ammonia=90:10:1)
Mass spectrum (ESI$^+$): m/z=432 [M+H]$^+$

(40) 1-(3-cyano-benzyl)-3-methyl-7-(2-butyn-1-yl)-8-((R)-3-amino-piperidin-1-yl)-xanthine (BOC cleaving carried out with trifluoroacetic acid)
$R_f$ value: 0.40 (silica gel, methylene chloride/methanol/conc. aqueous ammonia=90:10:1)
Mass spectrum (ESI$^+$): m/z=432 [M+H]$^+$

(41) 1-(4-cyano-benzyl)-3-methyl-7-(2-butyn-1-yl)-8-((R)-3-amino-piperidin-1-yl)-xanthine (BOC cleaving carried out with trifluoroacetic acid)
$R_f$ value: 0.31 (silica gel, methylene chloride/methanol/conc. aqueous ammonia=90:10:1)
Mass spectrum (ESI$^+$): m/z=432 [M+H]$^+$

(42) 1-[(pyridin-2-yl)methyl]-3-methyl-7-(2-butyn-1-yl)-8-((R)-3-amino-piperidin-1-yl)-xanthine $R_f$ value: 0.52 (silica gel, methylene chloride/methanol/conc. aqueous ammonia=90:10:1)
Mass spectrum (ESI$^+$): m/z=408 [M+H]$^+$

(43) 1-benzyl-3-methyl-7-(2-butyn-1-yl)-8-((R)-3-amino-piperidin-1-yl)-xanthine (BOC cleaving carried out with trifluoroacetic acid)
melting point: 207-209° C.
Mass spectrum (ESI$^+$): m/z=407 [M+H]$^+$

(44) 1-(4-methoxy-benzyl)-3-methyl-7-(2-butyn-1-yl)-8-((R)-3-amino-piperidin-1-yl)-xanthine-hydrochloride $R_f$ value: 0.50 (silica gel, methylene chloride/methanol/conc. aqueous ammonia=90:10:0.1)
Mass spectrum (ESI$^+$): m/z=437 [M+H]$^+$

(45) 1-(2-chloro-benzyl)-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)
Mass spectrum (ESI$^+$): m/z=441, 443 [M+H]$^+$

(46) 1-(2,6-dicyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=457 [M+H]$^+$

(47) 1-(2-cyano-4-bromo-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=510, 512 [M+H]$^+$

(48) 1-(3-fluoro-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=425 [M+H]$^+$

(49) 1-(3,5-dimethoxy-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=467 [M+H]$^+$

(50) 1-(2-fluoro-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=425 [M+H]$^+$

(51) 1-[(6-cyano-pyridin-2-yl)methyl]-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=433 [M+H]$^+$

(52) 1-[(3-cyano-pyridin-2-yl)methyl]-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=433 [M+H]$^+$

(53) 1-(2-cyano-3-chloro-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=466, 468 [M+H]$^+$

(54) 1-(4-fluoro-benzyl)-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=425 [M+H]$^+$

(55) 1-(4-chloro-benzyl)-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=441, 443 [M+H]$^+$

(56) 1-(2-cyano-4-fluoro-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=450 [M+H]$^+$

(57) 1-(3-cyano-4-fluoro-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=450 [M+H]$^+$

(58) 1-(2-chloro-4-cyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=466, 468 [M+H]$^+$

(59) 1-[(5-methoxycarbonyl-furan-2-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=455 [M+H]$^+$

(60) 1-(2-trifluoromethyl-4-cyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=500 [M+H]$^+$

(61) 1-(3,5-dicyano-benzyl)-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=457 [M+H]$^+$

(62) 1-(3-nitro-4-cyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=477 [M+H]$^+$

(63) 1-[(2-cyano-pyridin-3-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.50 (reversed phase ready-made TLC plate (E. Merck), acetonitrile/water/trifluoroacetic acid=50:50:1)
Mass spectrum (ESI$^+$): m/z=433 [M+H]$^+$

(64) 1-(2-cyano-4-methoxy-benzyl)-3-methyl-7-(2-butyn-1-yl)-8-((R)-3-amino-piperidin-1-yl)-xanthine (BOC cleaving carried out with trifluoroacetic acid)
$R_f$ value: 0.50 (reversed phase ready-made TLC plate (E. Merck), acetonitrile/water/trifluoroacetic acid=50:50:1)
Mass spectrum (ESI$^+$): m/z=462 [M+H]$^+$

(65) 1-(2-cyano-5-methoxy-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (reversed phase ready-made TLC plate (E. Merck), acetonitrile/water/trifluoroacetic acid=50:50:1)
Mass spectrum (ESI$^+$): m/z=462 [M+H]$^+$

(66) 1-(3-methoxy-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=437 [M+H]$^+$

(67) 1-(3-trifluoromethyl-benzyl)-3-methyl-7-(2-butyn-1-yl)-8-((R)-3-amino-piperidin-1-yl)-xanthine (BOC cleaving carried out with trifluoroacetic acid)
$R_f$ value: 0.60 (silica gel, methylene chloride/methanol/conc. aqueous ammonia=90:10:0.1)
Mass spectrum (ESI$^+$): m/z=475 [M+H]$^+$

(68) 1-(3,4-dimethoxy-benzyl)-3-methyl-7-(2-butyn-1-yl)-8-((R)-3-amino-piperidin-1-yl)-xanthine (BOC cleaving carried out with trifluoroacetic acid)
$R_f$ value: 0.50 (silica gel, methylene chloride/methanol/conc. aqueous ammonia=90:10:0.1)
Mass spectrum (ESI$^+$): m/z=467 [M+H]$^+$

(69) 1-(3-chloro-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=441, 443 [M+H]$^+$

(70) 1-(4-trifluoromethyl-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=475 [M+H]$^+$

(71) 1-[([2,2']bipyridinyl-6-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)
Mass spectrum (ESI$^+$): m/z=485 [M+H]$^+$

(72) 1-(3,4-dimethoxy-6-fluoro-benzyl)-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)
Mass spectrum (ESI$^+$): m/z=485 [M+H]$^+$

(73) 1-[(6-fluoro-pyridin-2-yl)methyl]-3-methyl-7-(2-butyn-1-yl)-8-((R)-3-amino-piperidin-1-yl)-xanthine $R_f$ value: 0.41 (silica gel, methylene chloride/methanol/conc. aqueous ammonia=90:10:1)
Mass spectrum (ESI$^+$): m/z=426 [M+H]$^+$

(74) 1-[(5-cyano-6-methoxy-pyridin-2-yl)methyl]-3-methyl-7-(2-butyn-1-yl)-8-((R)-3-amino-piperidin-1-yl)-xanthine $R_f$ value: 0.40 (silica gel, methylene chloride/methanol/conc. aqueous ammonia=90:10:1)
Mass spectrum (ESI$^+$): m/z=463 [M+H]$^+$

(75) 1-(2,6-difluoro-benzyl)-3-methyl-7-(2-butyn-1-yl)-8-((R)-3-amino-piperidin-1-yl)-xanthine $R_f$ value: 0.41 (silica gel, methylene chloride/methanol/conc. aqueous ammonia=90:10:1)
Mass spectrum (ESI$^+$): m/z=443 [M+H]$^+$

(76) 1-(3-trifluoromethoxy-benzyl)-3-methyl-7-(2-butyn-1-yl)-8-((R)-3-amino-piperidin-1-yl)-xanthine $R_f$ value: 0.36 (silica gel, methylene chloride/methanol/conc. aqueous ammonia=90:10:1)
Mass spectrum (ESI$^+$): m/z=491 [M+H]$^+$

(77) 1-(4-trifluoromethoxy-benzyl)-3-methyl-7-(2-butyn-1-yl)-8-((R)-3-amino-piperidin-1-yl)-xanthine $R_f$ value: 0.38 (silica gel, methylene chloride/methanol/conc. aqueous ammonia=90:10:1)
Mass spectrum (ESI$^+$): m/z=491 [M+H]$^+$

(78) 1-[(2-cyano-pyridin-4-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.60 (reversed phase ready-made TLC plate (E. Merck), acetonitrile/water/trifluoroacetic acid=50:50:1)
Mass spectrum (ESI$^+$): m/z=433 [M+H]$^+$

(79) 1-[(5-cyano-pyridin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.60 (reversed phase ready-made TLC plate (E. Merck), acetonitrile/water/trifluoroacetic acid=50:50:1)
Mass spectrum (ESI$^+$): m/z=433 [M+H]$^+$

(80) 1-[(pyrimidin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.60 (reversed phase ready-made TLC plate (E. Merck), acetonitrile/water/trifluoroacetic acid=50:50:1)
Mass spectrum (ESI$^+$): m/z=409 [M+H]$^+$

(81) 1-[(4-methyl-pyrimidin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.65 (reversed phase ready-made TLC plate (E. Merck), acetonitrile/water/trifluoroacetic acid=50:50:1)
Mass spectrum (ESI$^+$): m/z=423 [M+H]$^+$

(82) 1-[(4,6-dimethyl-pyrimidin-2-yl)methyl]-3-methyl-7-(2-butyn-1-yl)-8-((R)-3-amino-piperidin-1-yl)-xanthine (BOC cleaving carried out with trifluoroacetic acid)
melting point: 202-204° C.
Mass spectrum (ESI$^+$): m/z=437 [M+H]$^+$

(83) 1-[(quinoxalin-6-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)
Mass spectrum (ESI$^+$): m/z=459 [M+H]$^+$

(84) 1-(3-fluoro-4-methoxy-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=455 [M+H]$^+$

(85) 1-(3,4-difluoro-benzyl)-3-methyl-7-(2-butyn-1-yl)-8-((R)-3-amino-piperidin-1-yl)-xanthine (BOC cleaving carried out with trifluoroacetic acid)
$R_f$ value: 0.45 (silica gel, methylene chloride/methanol/conc. aqueous ammonia=90:10:0.1)
Mass spectrum (ESI$^+$): m/z=443 [M+H]$^+$

(86) 1-(2-fluoro-5-methoxy-benzyl)-3-methyl-7-(2-butyn-1-yl)-8-((R)-3-amino-piperidin-1-yl)-xanthine $R_f$ value: 0.39 (silica gel, methylene chloride/methanol/conc. aqueous ammonia=90:10:1)
Mass spectrum (ESI$^+$): m/z=455 [M+H]$^+$

(87) 1-(2-fluoro-3-methoxy-benzyl)-3-methyl-7-(2-butyn-1-yl)-8-((R)-3-amino-piperidin-1-yl)-xanthine $R_f$ value: 0.41 (silica gel, methylene chloride/methanol/conc. aqueous ammonia=90:10:1)
Mass spectrum (ESI$^+$): m/z=455 [M+H]$^+$

(88) 1-[(4-cyano-isoquinolin-3-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.40 (silica gel, methylene chloride/methanol/conc. aqueous ammonia=90:10:0.1)
Mass spectrum (ESI$^+$): m/z=483 [M+H]$^+$

(89) 1-(2-fluoro-4-methoxy-benzyl)-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:1)
Mass spectrum (ESI$^+$): m/z=455 [M+H]$^+$

(90) 1-[(furan-2-yl)methyl]-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=397 [M+H]$^+$

(91) 1-(3,4-dicyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=457 [M+H]$^+$

(92) 1-[(furan-3-yl)methyl]-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=397 [M+H]$^+$

(93) 1-[(5-methyl-furan-2-yl)methyl]-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=411 [M+H]$^+$

(94) 1-[(5-bromo-furan-2-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=475, 477 [M+H]$^+$

(95) 1-(4-cyano-2-fluoro-benzyl)-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=450 [M+H]$^+$

(96) 1-(2-cyano-5-fluoro-benzyl)-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=450 [M+H]$^+$

(97) 1-[(5-cyano-furan-2-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)
Mass spectrum (ESI$^+$): m/z=422 [M+H]$^+$

(98) 1-(2-cyano-6-fluoro-benzyl)-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=450 [M+H]$^+$

(99) 1-(4-cyano-3-fluoro-benzyl)-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=450 [M+H]$^+$ (100) 1-(2-cyano-3-methoxy-benzyl)-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)
Mass spectrum (ESI$^+$): m/z=462 [M+H]$^+$ (101) 1-[(8-cyano-quinolin-7-yl)methyl]-3-methyl-7-(2-butyn-1-yl)-8-((R)-3-amino-piperidin-1-yl)-xanthine (BOC cleaving carried out with trifluoroacetic acid)
Mass spectrum (ESI$^+$): m/z=483 [M+H]$^+$ (102) 1-[(4-cyano-pyridin-3-yl)methyl]-3-methyl-7-(2-butyn-1-yl)-8-((R)-3-amino-piperidin-1-yl)-xanthine (BOC cleaving carried out with trifluoroacetic acid)
melting point: 166° C.
Mass spectrum (ESI$^+$): m/z=433 [M+H]$^+$ (103) 1-[(8-cyano-quinolin-2-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.50 (silica gel, methylene chloride/methanol/conc. aqueous ammonia=90:10:0.1)
Mass spectrum (ESI$^+$): m/z=483 [M+H]$^+$ (104) 1-[(1-methyl-1H-benzotriazol-5-yl)methyl]-3-methyl-7-(2-butyn-1-yl)-8-((R)-3-amino-piperidin-1-yl)-xanthine (BOC cleaving carried out with trifluoroacetic acid)
$R_f$ value: 0.60 (reversed phase ready-made TLC plate (E. Merck), acetonitrile/water/trifluoroacetic acid=50:50:1)
Mass spectrum (ESI$^+$): m/z=462 [M+H]$^+$ (105) 1-[(3-cyano-pyridin-4-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)
$R_f$ value: 0.65 (reversed phase ready-made TLC plate (E. Merck), acetonitrile/water/trifluoroacetic acid=50:50:1)
Mass spectrum (ESI$^+$): m/z=433 [M+H]$^+$ (106) 1-[(3-cyano-pyridin-2-yl)methyl]-3-methyl-7-(2-butyn-1-yl)-8-((S)-3-amino-piperidin-1-yl)-xanthine (BOC cleaving carried out with trifluoroacetic acid)
$R_f$ value: 0.60 (reversed phase ready-made TLC plate (E. Merck), acetonitrile/water/trifluoroacetic acid=50:50:1)
Mass spectrum (ESI$^+$): m/z=433 [M+H]$^+$ (107) 1-[(4-cyano-benzo[1,3]dioxol-5-yl)methyl]-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:0.1)
Mass spectrum (ESI$^+$): m/z=476 [M+H]$^+$ The following compounds may also be obtained analogously to the foregoing Examples and other methods known from the literature (1) 1-(2-cyano-4-fluoro-benzyl)-3-methyl-7-(2-butyn-1-yl)-8-((R)-3-amino-piperidin-1-yl)-xanthine
(2) 1-(2-cyano-5-fluoro-benzyl)-3-methyl-7-(2-butyn-1-yl)-8-((R)-3-amino-piperidin-1-yl)-xanthine
(3) 1-(2-cyano-6-fluoro-benzyl)-3-methyl-7-(2-butyn-1-yl)-8-((R)-3-amino-piperidin-1-yl)-xanthine
(4) 1-(3-cyano-4-fluoro-benzyl)-3-methyl-7-(2-butyn-1-yl)-8-((R)-3-amino-piperidin-1-yl)-xanthine
(5) 1-(3,5-dicyano-benzyl)-3-methyl-7-(2-butyn-1-yl)-8-((R)-3-amino-piperidin-1-yl)-xanthine
(6) 1-(3,4-dicyano-benzyl)-3-methyl-7-(2-butyn-1-yl)-8-((R)-3-amino-piperidin-1-yl)-xanthine
(7) 1-(3-nitro-4-cyano-benzyl)-3-methyl-7-(2-butyn-1-yl)-8-((R)-3-amino-piperidin-1-yl)-xanthine
(8) 1-(2-chloro-4-cyano-benzyl)-3-methyl-7-(2-butyn-1-yl)-8-((R)-3-amino-piperidin-1-yl)-xanthine
(9) 1-(2-fluoro-4-cyano-benzyl)-3-methyl-7-(2-butyn-1-yl)-8-((R)-3-amino-piperidin-1-yl)-xanthine
(10) 1-(2-trifluoromethyl-4-cyano-benzyl)-3-methyl-7-(2-butyn-1-yl)-8-((R)-3-amino-piperidin-1-yl)-xanthine
(11) 1-[(5-cyano-pyridin-2-yl)methyl]-3-methyl-7-(2-butyn-1-yl)-8-((R)-3-amino-piperidin-1-yl)-xanthine
(12) 1-[(4-cyano-pyridin-2-yl)methyl]-3-methyl-7-(2-butyn-1-yl)-8-((R)-3-amino-piperidin-1-yl)-xanthine
(13) 1-[(4-cyano-pyridin-3-yl)methyl]-3-methyl-7-(2-butyn-1-yl)-8-((R)-3-amino-piperidin-1-yl)-xanthine
(14) 1-[(3-cyano-pyridin-4-yl)methyl]-3-methyl-7-(2-butyn-1-yl)-8-((R)-3-amino-piperidin-1-yl)-xanthine
(15) 1-[(2-cyano-pyridin-3-yl)methyl]-3-methyl-7-(2-butyn-1-yl)-8-((R)-3-amino-piperidin-1-yl)-xanthine
(16) 1-[(2-cyano-pyridin-4-yl)methyl]-3-methyl-7-(2-butyn-1-yl)-8-((R)-3-amino-piperidin-1-yl)-xanthine
(17) 1-[(5-cyano-pyridin-3-yl)methyl]-3-methyl-7-(2-butyn-1-yl)-8-((R)-3-amino-piperidin-1-yl)-xanthine
(18) 1-[(6-cyano-pyridin-3-yl)methyl]-3-methyl-7-(2-butyn-1-yl)-8-((R)-3-amino-piperidin-1-yl)-xanthine
(19) 1-(2-cyano-4-methoxy-benzyl)-3-methyl-7-(2-butyn-1-yl)-8-((R)-3-amino-piperidin-1-yl)-xanthine
(20) 1-(2-cyano-5-methoxy-benzyl)-3-methyl-7-(2-butyn-1-yl)-8-((R)-3-amino-piperidin-1-yl)-xanthine
(21) 1-[([2,2']bipyridinyl-6-yl)methyl]-3-methyl-7-(2-butyn-1-yl)-8-((R)-3-amino-piperidin-1-yl)-xanthine
(22) 1-[(5-methoxy-pyridin-2-yl)methyl]-3-methyl-7-(2-butyn-1-yl)-8-((R)-3-amino-piperidin-1-yl)-xanthine
(23) 1-[(6-fluoro-pyridin-2-yl)methyl]-3-methyl-7-(2-butyn-1-yl)-8-((R)-3-amino-piperidin-1-yl)-xanthine
(24) 1-[(5-cyano-6-methoxy-pyridin-2-yl)methyl]-3-methyl-7-(2-butyn-1-yl)-8-((R)-3-amino-piperidin-1-yl)-xanthine
(25) 1-(2-methoxy-benzyl)-3-methyl-7-(2-butyn-1-yl)-8-((R)-3-amino-piperidin-1-yl)-xanthine
(26) 1-(3-methoxy-benzyl)-3-methyl-7-(2-butyn-1-yl)-8-((R)-3-amino-piperidin-1-yl)-xanthine
(27) 1-(3-chloro-benzyl)-3-methyl-7-(2-butyn-1-yl)-8-((R)-3-amino-piperidin-1-yl)-xanthine
(28) 1-(4-trifluoromethyl-benzyl)-3-methyl-7-(2-butyn-1-yl)-8-((R)-3-amino-piperidin-1-yl)-xanthine
(29) 1-(3-trifluoromethyl-benzyl)-3-methyl-7-(2-butyn-1-yl)-8-((R)-3-amino-piperidin-1-yl)-xanthine
(30) 1-(2-trifluoromethyl-benzyl)-3-methyl-7-(2-butyn-1-yl)-8-((R)-3-amino-piperidin-1-yl)-xanthine
(31) 1-(3,4-dimethoxy-benzyl)-3-methyl-7-(2-butyn-1-yl)-8-((R)-3-amino-piperidin-1-yl)-xanthine
(32) 1-(3,4-dimethoxy-6-fluoro-benzyl)-3-methyl-7-(2-butyn-1-yl)-8-((R)-3-amino-piperidin-1-yl)-xanthine
(33) 1-[(benzo[1,3]dioxol-5-yl)methyl]-3-methyl-7-(2-butyn-1-yl)-8-((R)-3-amino-piperidin-1-yl)-xanthine

EXAMPLE 2

Coated Tablets Containing 75 mg of Active Substance
1 Tablet Core Contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:
The active substance is mixed with calcium phosphate, corn starch, polyvinylpyrrolidone, hydroxypropylmethylcellulose and half the specified amount of magnesium stearate.

Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| | |
|---|---|
| Weight of core: | 230 mg |
| Die: | 9 mm, convex |

The tablet cores thus produced are coated with a film consisting essentially of hydroxypropylmethylcellulose. The finished film-coated tablets are polished with beeswax.

| | |
|---|---|
| Weight of coated tablet: | 245 mg. |

EXAMPLE 3

Tablets Containing 100 mg of Active Substance
Composition:
1 Tablet Contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Preparation:
The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

EXAMPLE 4

Tablets Containing 150 mg of Active Substance
Composition:
1 Tablet Contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:
The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| Die: | 10 mm, flat |

EXAMPLE 5

Hard Gelatine Capsules Containing 150 mg of Active Substance
1 Capsule Contains:

| | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:
The active substance is mixed with the excipients, passed through a screen with a mesh size of 0.75 mm and homogeneously mixed using a suitable apparatus. The finished mixture is packed into size 1 hard gelatine capsules.

| | |
|---|---|
| Capsule filling: | approx. 320 mg |
| Capsule shell: | size 1 hard gelatine capsule. |

EXAMPLE 6

Suppositories Containing 150 mg of Active Substance
1 Suppository Contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

EXAMPLE 7

Suspension Containing 50 mg of Active Substance
100 ml of Suspension Contain:

| | |
|---|---|
| active substance | 1.00 g |
| carboxymethylcellulose-Na-salt | 0.10 g |

-continued

| | |
|---|---|
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavoring | 0.30 g |
| dist. water | ad 100.00 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavoring have been added and dissolved, the suspension is evacuated with stirring to eliminate air.

5 ml of suspension contains 50 mg of active substance.

EXAMPLE 8

Ampoules Containing 10 mg Active Substance
Composition:

| | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 9

Ampoules Containing 50 mg of Active Substance
Composition:

| | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:
1. A process for preparing a compound of the formula (I)

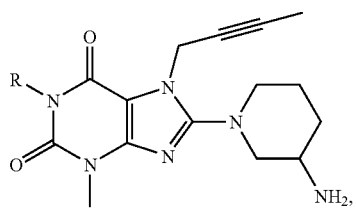

(I)

the process comprising:
reacting a compound of the formula (II)

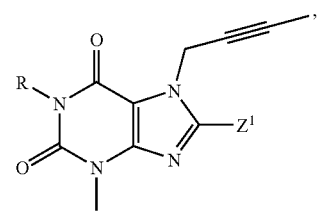

(II)

with 3-aminopiperidine, the enantiomers, or the salts thereof, wherein:
R is a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group,
a 2-trifluoromethyl-benzyl, 3-trifluoromethyl-benzyl or 4-trifluoromethyl-benzyl group,
a 3-trifluoromethoxy-benzyl, or 4-trifluoromethoxy-benzyl group,
a 2-cyanobenzyl, 3-cyanobenzyl, or 4-cyanobenzyl group,
a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group,
a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzl, or 3,4-dimethoxy-6-fluoro-benzyl group,
a (benzo[1,3]dioxol-5-yl)methyl group,
a [(4-cyano-benzo[1,3]dioxol-5-yl)methyl group,
a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group,
a 2-oxo-2-[2-(pyridin-3-yl)-phenyl]-ethyl or 2-oxo-2-[2-(pyridin-4-yl)-phenyl]-ethyl group,
a (3-cyano-naphthalen-1-yl)methyl, (1,4-dicyano-naphthalen-2-yl)methyl, or (2,4-dimethoxy-naphthalen-1-yl) methyl group,
a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group,
a (pyridin-2-yl)methyl, (6-fluoro-pyridin-2-yl)methyl, or (5-methoxy-pyridin-2-yl)methyl group,
a (3-cyanopyridin-2-yl)methyl, (6-cyanopyridin-2-yl) methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group,
a (6-phenyl-pyridin-2-yl)methyl or a ([2,2']bipyridinyl-6yl)methyl group,
a (pyrimidin-2-yl)methyl, (4-methyl-pyrimidin-2-yl) methyl, or (4,6-dimethyl-pyrimidin-2-yl)methyl group, a (2-phenyl-pyrimidin-4-yl)methyl or (4-phenyl-pyrimidin-2-yl)methyl group, a [(1-methyl-1H-benzotriazol-5-yl)methyl] group, a (6-fluoro-quinolin-2-yl)methyl, (7-fluoro-quinolin-2-yl)methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl)methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl)methyl, (6,7-dimethoxy-quinolin-2-yl)methyl, or (8-cyano-quinolin-7-yl)methyl group, a (1-cyano-isoquinolin-3-yl)methyl, (4-cyano-isoquinolin-1-yl)methyl-(4-cyano-isoquinolin-3-yl)methyl, or [(4-(pyridin-2-yl)-isoquinolin-1-yl]methyl group, a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl)methyl, (4-cyclopropyl-quinazolin-2-yl)methyl, (2-phenyl-quinazolin-4-yl)methyl, (4-cyano-quinazolin-2-yl)methyl, (4-phenylamino-quinazolin-2-yl)methyl, or (4-benzylamino-quinazolin-2-yl)methyl group, a (quinoxalin-5-yl)methyl-(quinoxalin-6-yl)methyl or (2,3-dimethyl-quinoxalin-6-yl)methyl group, or a ([1,5]naphthyridin-3-yl)methyl group, and $Z^1$ is a leaving group selected from a halogen atom mercapto, methanesulfonyl, and methanesulfonoxy group.

2. The process according to claim 1, wherein R is a (3-cyanopyridin-2-yl)methyl group.

3. A process for preparing a compound of the formula (I)

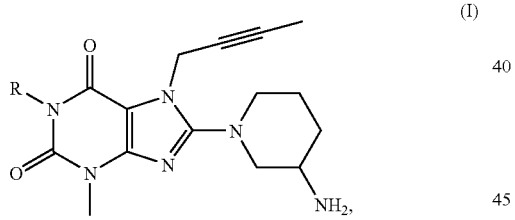

(I)

the process comprising:
deprotecting a compound of the formula (III)

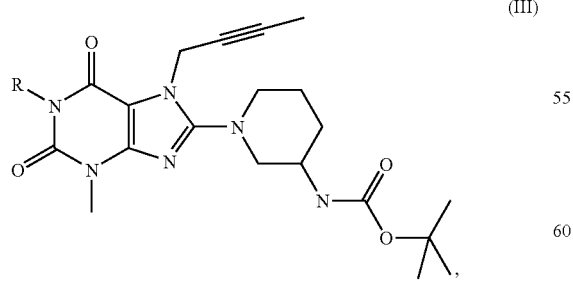

(III)

wherein:

R is a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group, a 2-trifluoromethyl-benzyl, 3-trifluoromethyl-benzyl or 4-trifluoromethyl-benzyl group, a 3-trifluoromethoxy-benzyl or 4-trifluoromethoxy-benzyl group, a 2-cyanobenzyl, 3-cyanobenzyl or 4-cyanobenzyl group, a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group, a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenz, or 3,4-dimethoxy-6-fluoro-benzyl group, a (benzo[1,3]dioxol-5-yl)methyl group, a [(4-cyano-benzo[1,3]dioxol5-yl)methyl group, a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group, a 2-oxo-2-[2-(pyridin-3-yl)-phenyl]-ethyl or 2-oxo-2-[2-(pyridin-4-yl)-phenyl]-ethyl group, a (3-cyano-naphthalen-1-yl)methyl, (1,4-dicyano-naphthalen-2-yl)methyl, or (2,4-dimethoxy-naphthalen-1-yl)methyl group, a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group, a (pyridin-2-yl)methyl, (6-fluoro-pyridin-2-yl)methyl, or (5-methoxy-pyridin-2-yl)methyl group, a (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group, a (6-phenyl-pyridin-2-yl)methyl or a ([2,2']bipyridinyl-6-yl)methyl group, a (pyrimidin-2-yl)methyl, (4-methyl-pyrimidin-2-yl)methyl, or (4,6-dimethyl-pyrimidin-2-yl)methyl group, a (2-phenyl-pyrimidin-4-yl)methyl or (4-phenyl-pyrimidin-2-yl)methyl group, a [(1-methyl-1H-benzotriazol-5-yl)methyl] group, a (6-fluoro-quinolin-2-yl)methyl, (7-fluoro-quinolin-2-yl)methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl)methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl)methyl, (6,7-dimethoxy-quinolin-2-yl)methyl, or (8-cyano-quinolin-7-yl)methyl group, a (1-cyano-isoquinolin-3-yl)methyl, (4-cyano-isoquinolin-1-yl)methyl-(4-cyano-isoquinolin-3-yl)methyl, or [(4-(pyridin-2-yl)-isoquinolin-1-yl]methyl group, a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl)methyl, (4-cyclopropyl-quinazolin-2-yl)methyl, (2-phenyl-quinazolin-4-yl)methyl, (4-cyano-quinazolin-2-yl)methyl, (4-phenylamino-quinazolin-2-yl)methyl, or (4-benzylamino-quinazolin-2-yl)methyl group, a (quinoxalin-5-yl)methyl-(quinoxalin-6-yl)methyl or (2,3-dimethyl-quinoxalin-6-yl)methyl group, or a ([1,5]naphthyridin-3-yl)methyl group.

4. The process according to claim 3, wherein R is a (3-cyanopyridin-2-yl)methyl group.

5. A process for preparing a compound of the formula (Ia)

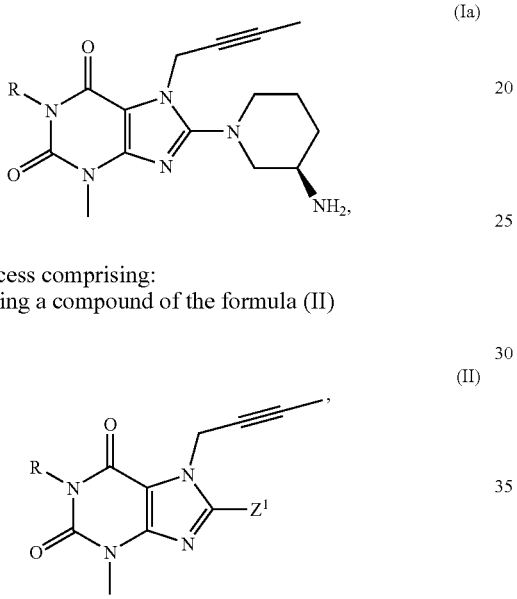

(Ia)

the process comprising:
reacting a compound of the formula (II)

(II)

with (R)-3aminopiperidine, or the salts thereof, wherein:
R is a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group, a 2-trifluoromethyl-benzyl, 3-trifluoromethyl-benzl, or 4-trifluoromethyl-benzyl group, a 3-trifluoromethoxy-benzyl or 4-trifluoromethoxy-benzyl group, a 2-cyanobenzyl, 3-cyanobenzyl, or 4-cyanobenzyl group, a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group, a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzl, or 3,4-dimethoxy-6-fluoro-benzyl group, a (benzo[1,3]dioxol-5-yl)methyl group, a [(4-cyano-benzo[1,3]dioxol-5-yl)methyl] group, a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group, a 2-oxo-2-[2-(pyridin-3-yl)-phenyl]-ethyl or 2-oxo-2-[2-(pyridin-4-yl)-phenyl]-ethyl group, a (3-cyano-naphthalen-1-yl)methyl, (1,4-dicyano-naphthalen-2-yl)methyl, or (2,4-dimethoxy-naphthalen-1-yl)methyl group, a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group, a (pyridin-2-yl)methyl, (6-fluoro-pyridin-2-yl)methyl, or (5-methoxy-pyridin-2-yl)methyl group, a (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group, a (6-phenyl-pyridin-2-yl)methyl or a ([2,2']bipyridinyl-6-yl)methyl group, a (pyrimidin-2-yl)methyl, (4-methyl-pyrimidin-2-yl)methyl, or (4,6-dimethyl-pyrimidin-2-yl)methyl group, a (2-phenyl-pyrimidin-4-yl)methyl or (4-phenyl-pyrimidin-2-yl)methyl group, a [(1-methyl-1H-benzotriazol-5-yl)methyl] group, a (6-fluoro-quinolin-2-yl)methyl, (7-fluoro-quinolin-2-yl)methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl)methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl)methyl, (6,7-dimethoxy-quinolin-2-yl)methyl, or (8-cyano-quinolin-7-yl)methyl group, a (1-cyano-isoquinolin-3-yl)methyl, (4-cyano-isoquinolin-1-yl)methyl-(4-cyano-isoquinolin-3-yl)methyl, or [(4-(pyridin-2-yl)-isoquinolin-1-yl]methyl group, a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl)methyl, (4-cyclopropyl-quinazolin-2-yl)methyl, (2-phenyl-quinazolin-4-yl)methyl, (4-cyano-quinazolin-2-yl)methyl, (4-phenylamino-quinazolin-2-yl)methyl, or (4-benzylamino-quinazolin-2-yl)methyl group, a (quinoxalin-5-yl)methyl-(quinoxalin-6-yl)methyl or (2,3-dimethyl-quinoxalin-6-yl)methyl group, or a ([1,5]naphthyridin-3-yl)methyl group, and $Z^1$ is a leaving group selected from a halogen atom, mercapto, Methanesulfonyl, and methanesulfonoxy group.

6. A process for preparing a compound of the formula (Ia)

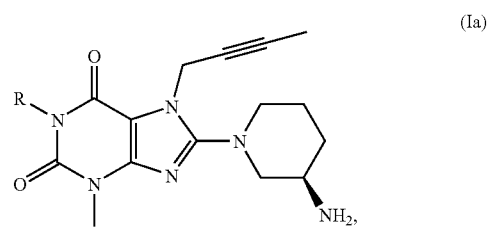

(Ia)

the process comprising:
deprotecting a compound of the formula (III)

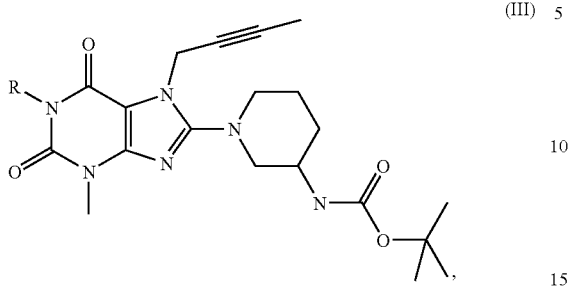

(III)

wherein:
R is a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group,
a 2-trifluoromethyl-benzyl, 3-trifluoromethyl-benzyl, or 4-trifluoromethyl-benzyl group,
a 3-trifluoromethoxy-benzyl or 4-trifluoromethoxy-benzyl group,
a 2-cyanobenzyl, 3-cyanobenzyl, or 4-cyanobenzyl group,
a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group,
a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl, or 3,4-dimethoxy-6-fluorobenzyl group,
a (benzo[1,3]dioxol-5-yl)methyl group,
a [(4-cyano-benzo[1,3]dioxol-5-yl)methyl] group,
a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group,
a 2-oxo-2-[2-(pyridin-3-yl)-phenyl]-ethyl or 2-oxo-2-[2-(pyridin-4-yl)-phenyl]-ethyl group,
a (3-cyano-naphthalen-1-yl)methyl, (1,4-dicyano-naphthalen-2-yl)methyl, or (2,4-dimethoxy-naphthalen-1-yl)methyl group,
a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group,
a (pyridin-2-yl)methyl, (6-fluoro-pyridin-2-yl)methyl, or (5-methoxy-pyridin-2-yl)methyl group,
a (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group,
a (6-phenyl-pyridin-2-yl)methyl or a ([2,2']bipyridinyl-6-yl)methyl group,
a (pyrimidin-2-yl)methyl, (4-methyl-pyrimidin-2-yl)methyl, or (4,6-dimethyl-pyrimidin-2-yl)methyl group,
a (2-phenyl-pyrimidin-4-yl)methyl or (4-phenyl-pyrimidin-2-yl)methyl group,
a [(1-methyl-1H-benzotriazol-5-yl)methyl] group,
a (6-fluoro-quinolin-2-yl)methyl, (7-fluoro-quinolin-2-yl)methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl)methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl)methyl, (6,7-dimethoxy-quinolin-2-yl)methyl, or (8-cyano-quinolin-7-yl)methyl group,
a (1-cyano-isoquinolin-3-yl)methyl, (4-cyano-isoquinolin-1-yl)methyl- (4-cyano-isoquinolin-3-yl)methyl, or [(4-(pyridin-2-yl)-isoquinolin-1-yl]methyl group,
a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl) methyl, (4-cyclopropyl-quinazolin-2-yl)methyl, (2-phenyl-quinazolin-4-yl)methyl, (4-cyano-quinazolin-2-yl)methyl, (4-phenylamino-quinazolin-2-yl)methyl, or (4-benzylamino-quinazolin-2-yl)methyl group,
a (quinoxalin-5-yl)methyl-(quinoxalin-6-yl)methyl or (2,3-dimethyl-quinoxalin-6-yl)methyl group, or
a ([1,5]naphthyridin-3-yl)methyl group.

7. A process for preparing a compound of the formula (Ib)

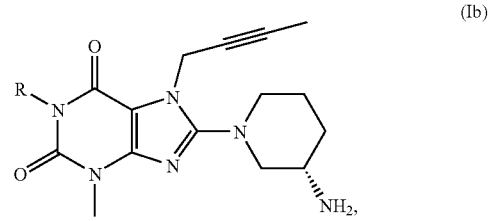

(Ib)

the process comprising:
reacting a compound of the formula (II)

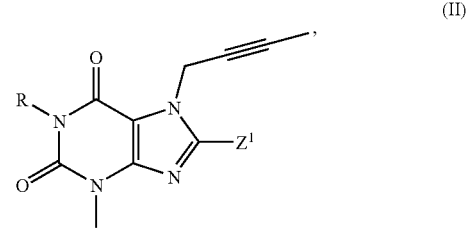

(II)

with (S)-3-aminopiperidine, or the salts thereof, wherein:
R is a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group,
a 2-trifluoromethyl-benzyl, 3-trifluoromethyl-benzyl, or 4-trifluoromethyl-benzyl group,
a 3-trifluoromethoxy-benzyl or 4-trifluoromethoxy-benzyl group, a 2-cyanobenzyl, 3-cyanobenzyl, or 4-cyanobenzyl group,
a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group,
a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl, or 3,4-dimethoxy-6-fluorobenzyl group,
a (benzo[1,3]dioxol-5-yl)methyl group,
a [(4-cyano-benzo[1,3]dioxol-5-yl)methyl group,
a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group,
a 2-oxo-2-[2-(pyridin-3-yl)-phenyl]-ethyl or 2-oxo-2-[2-(pyridin-4-yl)-phenyl]-ethyl group,
a (3-cyano-naphthalen-1-yl)methyl, (1,4-dicyano-naphthalen-2-yl)methyl, or (2,4-dimethoxy-naphthalen-1-yl)methyl group,
a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group,
a (pyridin-2-yl)methyl, (6-fluoro-pyridin-2-yl)methyl, or (5-methoxy-pyridin-2-yl)methyl group,
a (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group,
a (6-phenyl-pyridin-2-yl)methyl or a ([2,2']bipyridinyl-6-yl)methyl group,
a (pyrimidin-2-yl)methyl, (4-methyl-pyrimidin-2-yl)methyl, or (4,6-dimethyl-pyrimidin-2-yl)methyl group,
a (2-phenyl-pyrimidin-4-yl)methyl or (4-phenyl-pyrimidin-2-yl)methyl group,
a [(1-methyl-1H-benzotriazol-5-yl)methyl] group,
a (6-fluoro-quinolin-2-yl)methyl, (7-fluoro-quinolin-2-yl)methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl)methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl)methyl, (6,7-dimethoxy-quinolin-2-yl)methyl, or (8-cyano-quinolin-7-yl)methyl group,
a (1-cyano-isoquinolin-3-yl)methyl, (4-cyano-isoquinolin-1-yl)methyl-(4-cyano-isoquinolin-3-yl)methyl, or [(4-(pyridin-2-yl)-isoquinolin-1-yl)]methyl group,
a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl)methyl, (4-cyclopropyl-quinazolin-2-yl)methyl, (2-phenyl-quinazolin-4-yl)methyl, (4-cyano-quinazolin-2-yl)methyl, (4-phenylamino-quinazolin-2-yl)methyl, or (4-benzylamino-quinazolin-2-yl)methyl group,
a (quinoxalin-5-yl)methyl-(quinoxalin-6-yl)methyl or (2,3-dimethyl-quinoxalin-6-yl)methyl group, or
a ([1,5]naphthyridin-3-yl)methyl group, and
$Z^1$ is a leaving group selected from a halogen atom, mercapto, methanesulfonyl, and methanesulfonoxy group.

8. A process for preparing a compound of the formula (Ib)

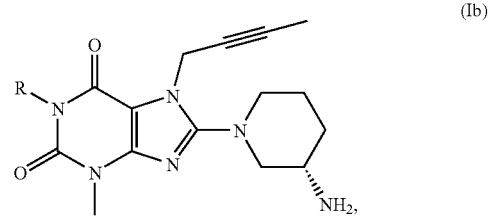

the process comprising:
deprotecting a compound of the formula (III):

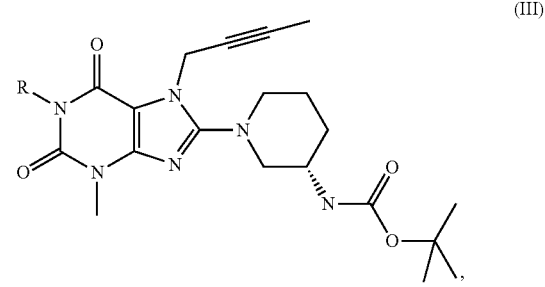

wherein:
R is a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group,
a 2-trifluoromethyl-benzyl, 3-trifluoromethyl-benzyl or 4-trifluoromethyl-benzyl group,
a 3-trifluoromethoxy-benzyl or 4-trifluoromethoxy-benzyl group,
a 2-cyanobenzyl, 3-cyanobenzyl or 4-cyanobenzyl group,
a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group,
a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl, or 3,4-dimethoxy-6-fluorobenzyl group,
a (benzo[1,3]dioxol-5-yl)methyl group,
a [(4-cyano-benzo[1,3]dioxol-5-yl)methyl group,
a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group, a 2-oxo-2-[2-(pyridin-3-yl)-phenyl]-ethyl or 2-oxo-2-[2-(pyridin-4-yl)-phenyl]-ethyl group, a (3-cyano-naphthalen-1-yl)methyl, (1,4-dicyano-naphthalen-2-yl)methyl, or (2,4-dimethoxy-naphthalen-1-yl)methyl group, a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group, a (pyridin-2-yl)methyl, (6-fluoro-pyridin-2-yl)methyl, or (5-methoxy-pyridin-2-yl)methyl group, a (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group, a (6-phenyl-pyridin-2-yl)methyl or a ([2,2']bipyridinyl-6-yl)methyl group, a (pyrimidin-2-yl)methyl, (4-methyl-pyrimidin-2-yl)methyl, or (4,6-dimethyl-pyrimidin-2-yl)methyl group, a (2-phenyl-pyrimidin-4-yl)methyl or (4-phenyl-pyrimidin-2-yl)methyl group, a [(1-methyl-1H-benzotriazol-5-yl)methyl] group, a (6-fluoro-quinolin-2-yl)methyl, (7-fluoro-quinolin-2-yl)methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl)methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl)methyl, (6,7-dimethoxy-quinolin-2-yl)methyl, or (8-cyano-quinolin-7-yl)methyl group, a (1-cyano-isoquinolin-3-yl)methyl, (4-cyano-isoquinolin-1-yl)methyl- (4-cyano-isoquinolin-3-yl)methyl, or [(4-(pyridin-2-yl)-isoquinolin-1-yl]methyl group, a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl)methyl, (4-cyclopropyl-quinazolin-2-yl)methyl, (2-phenyl-quinazolin-4-yl)methyl, (4-cyano-quinazolin-2-yl)methyl, (4-phenylamino-quinazolin-2-yl)methyl, or (4-benzylamino-quinazolin-2-yl)methyl group, a (quinoxalin-5-yl)methyl-(quinoxalin-6-yl)methyl or (2,3-dimethyl-quinoxalin-6-yl)methyl group, or a ([1,5]naphthyridin-3-yl) methyl group.

* * * * *